(12) United States Patent
Ram et al.

(10) Patent No.: US 10,912,474 B2
(45) Date of Patent: Feb. 9, 2021

(54) MICROELECTRONIC SENSOR FOR USE IN HYPERSENSITIVE MICROPHONES

(71) Applicant: EPITRONIC HOLDINGS PTE LTD., Singapore (SG)

(72) Inventors: Ayal Ram, Singapore (SG); Gideon Kapan, Zweibruecken (DE)

(73) Assignee: EPITRONIC HOLDINGS PTE LTD., Singapore (SG)

( * ) Notice: Subject to any disclaimer, the term of this patent is extended or adjusted under 35 U.S.C. 154(b) by 0 days.

(21) Appl. No.: 16/082,531

(22) PCT Filed: Mar. 7, 2017

(86) PCT No.: PCT/IB2017/051327
§ 371 (c)(1),
(2) Date: Oct. 10, 2018

(87) PCT Pub. No.: WO2017/153911
PCT Pub. Date: Sep. 14, 2017

(65) Prior Publication Data
US 2019/0069790 A1  Mar. 7, 2019

Related U.S. Application Data

(63) Continuation of application No. 15/067,093, filed on Mar. 10, 2016, now abandoned, and a continuation of
(Continued)

(51) Int. Cl.
*H01L 29/778* (2006.01)
*A61B 5/04* (2006.01)
(Continued)

(52) U.S. Cl.
CPC .......... *A61B 5/0408* (2013.01); *A61B 1/2736* (2013.01); *A61B 3/16* (2013.01);
(Continued)

(58) Field of Classification Search
CPC . H01L 29/2003; H01L 27/20; H01L 29/7783; H01L 29/66462; H01L 27/14806;
(Continued)

(56) References Cited

U.S. PATENT DOCUMENTS 4,965,697 A  10/1990  Mosser et al.
2002/0185655 A1* 12/2002 Fahimulla ............ B82Y 10/00
257/192

(Continued)

FOREIGN PATENT DOCUMENTS

WO  2013170018 A1  11/2013

OTHER PUBLICATIONS

Corekci et al. "Surface Morphology of Al0.3Ga0.7N/Al2O3-High Electron Mobility Transistor Structure" Journal of Nanoscience and Nanotechnology, vol. 8 Issue: 2 pp. 640-644, Feb. 2008. (Year: 2008).*

(Continued)

*Primary Examiner* — Joseph A Stoklosa
*Assistant Examiner* — Brian M Antiskay
(74) *Attorney, Agent, or Firm* — The Roy Gross Law Firm, LLC; Roy Gross

(57) ABSTRACT

In some embodiments, the PC-HEMT based microelectronic sensors are used in recording physiological and non-physiological sounds as hypersensitive microphones. Recording the physiological sounds is associated with the S1/S2 heart split phenomena and phonocardiography.

21 Claims, 18 Drawing Sheets
(15 of 18 Drawing Sheet(s) Filed in Color)

Related U.S. Application Data application No. 15/157,285, filed on May 17, 2016, now abandoned.

(60) Provisional application No. 62/384,831, filed on Sep. 8, 2016.

(51) Int. Cl.

| | | |
|---|---|---|
| *A61B 5/0408* | (2006.01) | |
| *H01L 29/205* | (2006.01) | |
| *H01L 29/20* | (2006.01) | |
| *A61B 5/00* | (2006.01) | |
| *A61B 5/0452* | (2006.01) | |
| *A61B 3/16* | (2006.01) | |
| *A61B 1/273* | (2006.01) | |
| *A61B 5/0478* | (2006.01) | |
| *A61B 7/04* | (2006.01) | |
| *G01N 27/414* | (2006.01) | |
| *A61B 5/08* | (2006.01) | |
| *A61B 5/11* | (2006.01) | |
| *A61B 5/021* | (2006.01) | |
| *A61B 5/05* | (2021.01) | |

(52) U.S. Cl.
CPC ........ *A61B 5/0006* (2013.01); *A61B 5/04017* (2013.01); *A61B 5/0452* (2013.01); *A61B 5/0478* (2013.01); *A61B 7/045* (2013.01); *G01N 27/414* (2013.01); *H01L 29/2003* (2013.01); *H01L 29/205* (2013.01); *H01L 29/7786* (2013.01); *A61B 5/002* (2013.01); *A61B 5/021* (2013.01); *A61B 5/05* (2013.01); *A61B 5/08* (2013.01); *A61B 5/1102* (2013.01); *A61B 5/1107* (2013.01); *A61B 5/681* (2013.01); *A61B 5/7225* (2013.01); *A61B 2562/164* (2013.01)

(58) Field of Classification Search
CPC ........... H01L 29/42316; H01L 21/8252; H01L 29/66212; H01L 29/872
USPC .......................................... 600/372, 382–393
See application file for complete search history.

(56) References Cited

U.S. PATENT DOCUMENTS

| | | | |
|---|---|---|---|
| 2004/0144991 A1* | 7/2004 | Kikkawa | H01L 29/66462 257/103 |
| 2007/0114568 A1* | 5/2007 | Simin | H01L 29/41725 257/192 |
| 2008/0265258 A1* | 10/2008 | Tanabe | H01L 29/66462 257/76 |
| 2009/0072272 A1* | 3/2009 | Suh | H01L 29/1066 257/194 |
| 2010/0036208 A1 | 2/2010 | Koh et al. | |
| 2010/0320505 A1* | 12/2010 | Okamoto | H01L 29/045 257/192 |
| 2011/0137184 A1 | 6/2011 | Ren et al. | |
| 2011/0199102 A1* | 8/2011 | Garcia | G01N 27/4148 324/658 |
| 2011/0213271 A1* | 9/2011 | Telfort | A61B 7/003 600/586 |
| 2014/0323895 A1* | 10/2014 | Vitushinsky | A61B 5/0408 600/523 |
| 2016/0029911 A1* | 2/2016 | Lee | A61B 5/02427 600/301 |
| 2017/0294528 A1* | 10/2017 | Ren | H01L 29/0657 |

OTHER PUBLICATIONS

Gassoumi et al. "Effect of surface passivation by SiN/SiO2 of AlGaN/GaN high-electron mobility transistors on Si substrate by deep level transient spectroscopy method" Semiconductor Physics and Technology (translated), 2013, vol. 47, Issue 7 2013. (Year: 2013).*

Vanko et al. "MEMS pressure sensor with an AlGaN/GaN based high electron mobility transistor" Tech Connect Briefs 2015 (Year: 2015).*

International Search Report PCT/IB2017/051327 Completed Jul. 21, 2017; dated Aug. 2, 2017 7 pages.

Written Opinion of the International Searching Authority PCT/IB2017/051327 dated Aug. 2, 2017 11 pages.

* cited by examiner $V_G \gg V_T$ $V_G = 0$
$V_G > V_T$ $V_G \ll V_T$

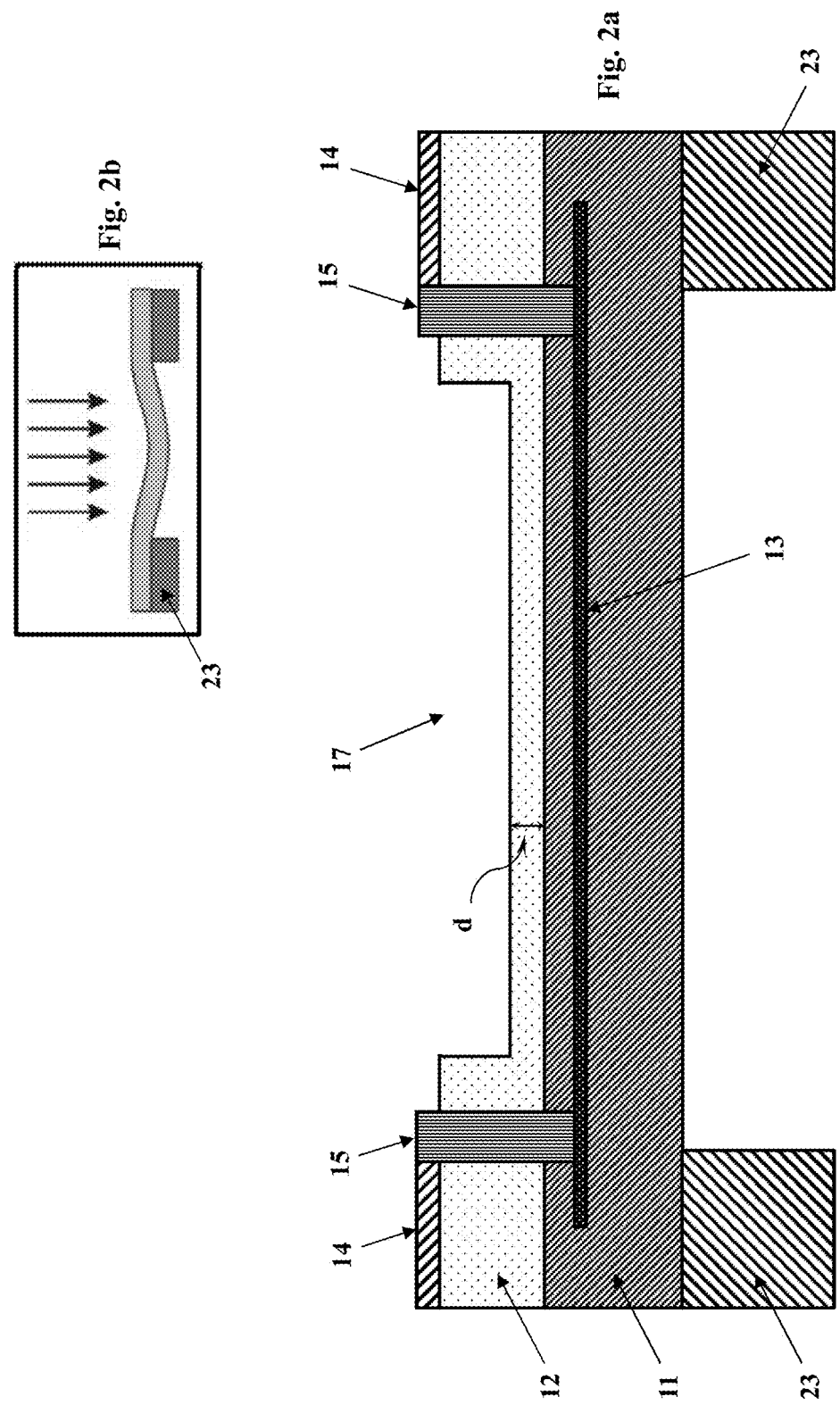

Fig. 6a          Ga-Face Polarity
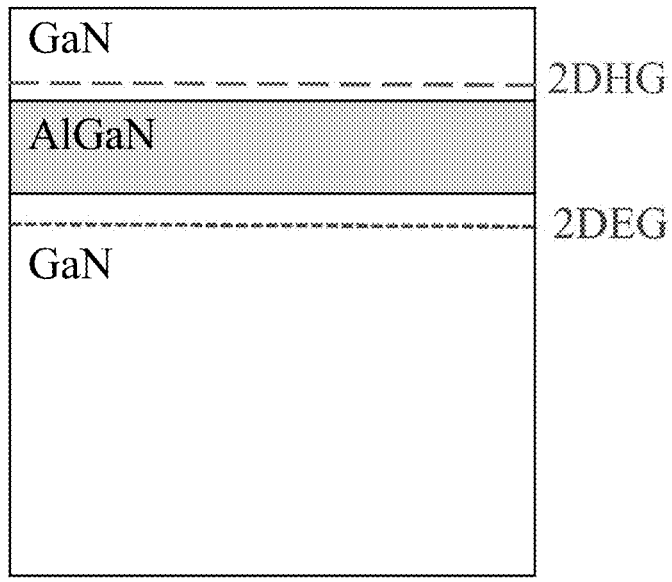
Fig. 6b          N-Face Polarity
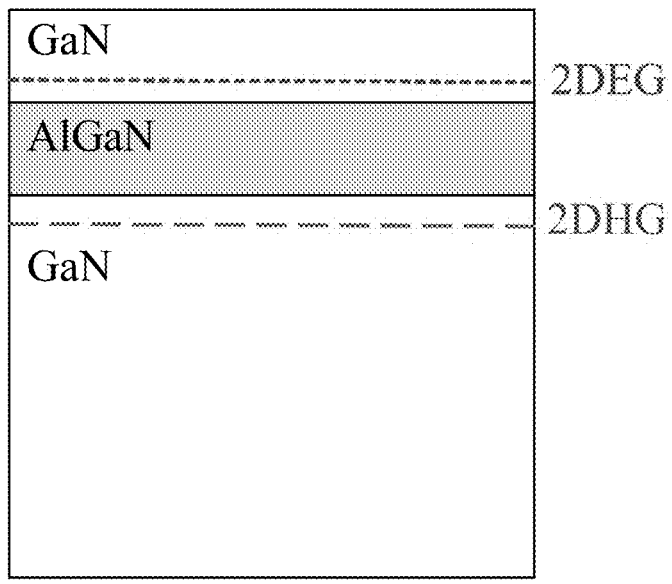

Fig. 8c
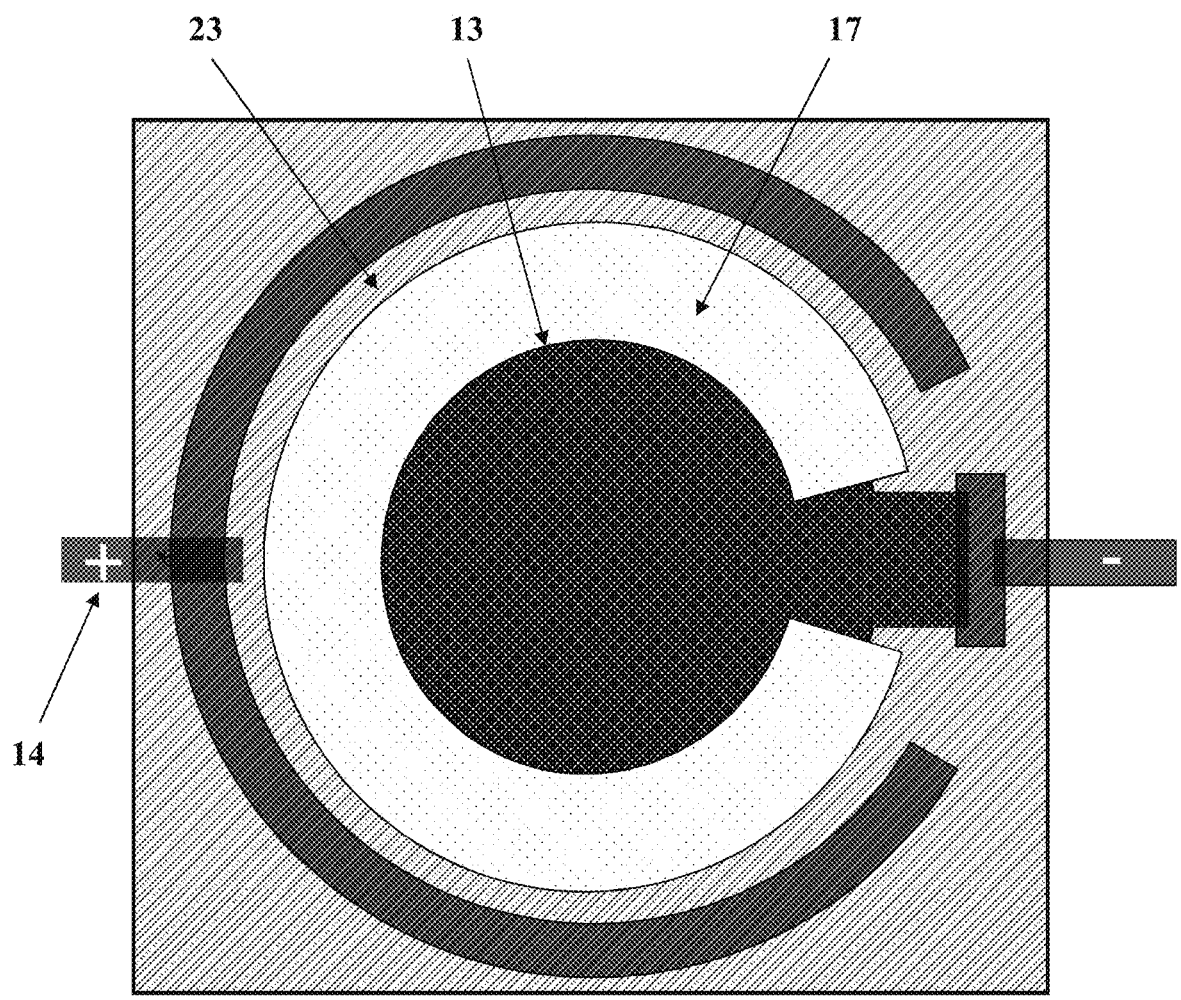
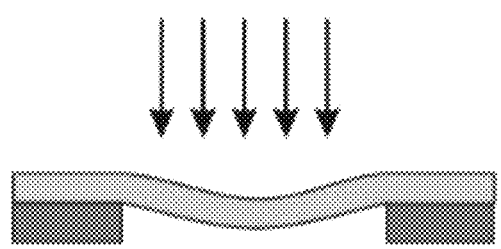

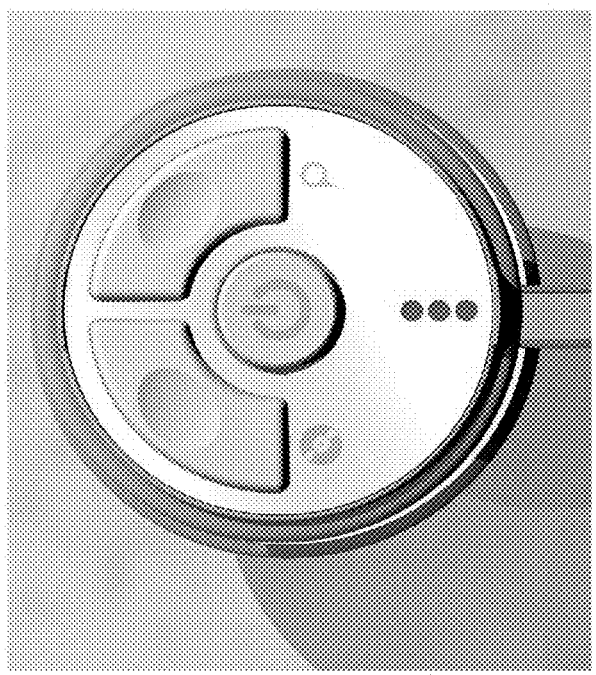
Fig. 11b

MICROELECTRONIC SENSOR FOR USE IN HYPERSENSITIVE MICROPHONES

RELATED APPLICATIONS

This application is a National Phase of PCT Patent Application No. PCT/IB2017/051327 having International filing date of Mar. 7, 2017, which claims the benefit of priority of U.S. patent application Ser. No. 15/067,093 filed on Mar. 10, 2016, U.S. patent application Ser. No. 15/157,285 filed on May 17, 2016, and U.S. Provisional Application No. 62/384,831 filed on Sep. 8, 2016. The contents of the above applications are all incorporated by reference as if fully set forth herein in their entirety.

TECHNICAL FIELD

The present application relates to the field of microelectronic sensors based on high-electron-mobility transistors. In particular, the present application relates to the open-gate pseudo-conductive high-electron-mobility transistors and their use in hypersensitive microphones.

BACKGROUND

Sensitivity of a microphone can be defined as a ratio of its analogue output voltage or digital output value to the input pressure, which is a major parameter of any microphone. Correlating signals in the acoustic domain to signals in the electrical domain can determine the magnitude of the microphone output signal with a known input.

Sensitivity of analogue microphones is straightforward and easy to measure. Typically defined in logarithmic units of dBV (decibels to 1V output voltage), it specifies how many volts the output signal will be for a given sound pressure level. The sensitivity of digital microphones defined in units of dBFS (decibels for digital full scale), is not that easy to measure. The difference in the measurement units points to an essential difference in the definition of sensitivity for digital microphones compared to that of their analogue brothers. For an analogue microphone with a relatively simple voltage output, the only limit to the size of the output signal is the practical limit of the voltage source supplying the voltage to the microphone. Although it is not practical, some analogue microphones might have as high as 20 dBV sensitivity with a 10V output signal. Such sensitivity could be easily accomplished as long as the electrical circuitry components, such as amplifiers or converters, could suffice supporting the required signal levels.

In contrast, sensitivity of a digital microphone is less flexible and much more problematic. It depends on a single parameter, which is a maximum acoustic input. As long as the full-scale digital sound is mapped to the maximum acoustic input of the digital microphone, the sensitivity becomes the difference between this input and the reference signal having 94 dB sound pressure level. For example, if the maximum sound pressure level of a digital microphone is 120 dB, then its sensitivity will be −26 dBFS, and there is absolutely no way to tweak the microphone's design to achieve the digital output signal higher for the given acoustic input, unless the maximum acoustic input is lowered by the same amount. The only way to overcome this problem is to conceptually change the way how the digital microphone records sounds. The present application therefore discloses a completely new approach to recording sounds by recording electrical signals associated with the sound waves.

High Electron Mobility Transistor

The polarization doped high-electron-mobility transistor (HEMT) is a field effect transistor (FET) in which two layers of different bandgap and polarisation field are grown upon each other forming a hetero-junction structure. As a consequence of the discontinuity in the polarisation field, surface charges are created at the interface between the layers of the hetero-junction structure. If the induced surface charge is positive, electrons will tend to compensate the induced charge resulting in the formation of the channel. Since in the HEMT, the channel electrons are confined in a quantum well in an infinitely narrow spatial region at the interface between the layers, these electrons are referred to as a two-dimensional electron gas (2DEG). This special confinement of the channel electrons in the quantum well actually grants them two-dimensional features, which strongly enhance their mobility surpassing the bulk mobility of the material in which the electrons are flowing.

The HEMTs based on the layers of III-V semiconductor materials, such as gallium nitride (GaN) and aluminium gallium nitride (AlGaN), have recently been developed with a view to high-voltage and high-power switching applications. The high voltages and high switching speeds allow smaller, more efficient devices, such as home appliances, communications and automobiles to be manufactured. To control the density of electrons in the 2DEG channel and to switch the HEMT on and off, the voltage at the gate of the transistor should be regulated.

FIGS. 1a-1c schematically shows the quantum well at three different biasing conditions starting from the positive gate potential ($V_G$), much higher than the threshold voltage ($V_T$), and going down to the 0V gate potential and further to the negative values below the threshold voltage. The $V_T$ is defined as a voltage required populating electrons at the interface between the GaN and AlGaN layers, thereby creating conductivity of the 2DEG channel. Since the 2DEG channel electrons occupy energy levels below the Fermi level, the Fermi level in a quantum well is located above several energy levels when $V_G \gg V_T$ (FIG. 1a). This enables high population of the 2DEG channel electrons and hence, high conductivity. The HEMT is turned on in this case. However, when $V_G$ decreases to 0V (FIG. 1b), the Fermi level also drops with respect to the quantum well. As a result, much fewer electron energy levels are populated and the amount of the 2DEG channel electrons significantly decreases. When $V_G \ll V_T$ (FIG. 1c), all electron energy levels are above the Fermi level, and there is no 2DEG electrons below the gate. This situation is called "channel depletion", and the HEMT is turned off.

Many commercially available AlGaN/GaN-based HEMT structures have a negative $V_T$, resulting in a "normally-on" operation mode at 0V gate potential. They are called "depletion-mode transistors" and used in various power switching applications when the negative voltage must be applied on the gate in order to block the current. However, for safe operation at high voltage or high power density, in order to reduce the circuit complexity and eliminate standby power consumption, HEMTs with "normally-off" characteristics are preferred.

Several techniques to manufacture the normally-off HEMTs have been reported. Burnham et al (2010) proposed normally-off structures of the recessed gate type. In this structure, the AlGaN barrier layer is etched and the gate is brought closer to the interface between the AlGaN barrier layer and the GaN buffer layer. As the gate approaches the interface between the layers, the $V_T$ increases. The normally-off operation of the transistor is achieved once the depletion region reaches the interface and depletes the 2DEG channel at zero gate voltage. The major advantages of these HEMTs are relatively lower power consumption, lower noise and simpler drive circuits. These HEMTs are currently used, for example, in microwave and millimetre wave communications, imaging and radars.

Chang et al (2009) proposed instead of etching the relatively thick barrier layer to approach the AlGaN/GaN interface, to use a very thin AlGaN barrier. This structure also achieves normally-off operation by approaching the gate towards the AlGaN/GaN interface. Chen et al (2010) proposed to use the fluorine-based plasma treatment method. Although many publications have adopted various methods to achieve normally-off devices with minimum impact on the drain current, they unfortunately sacrificed device turn-on performance.

SUMMARY

The present application describes embodiments of a microelectronic sensor, which is based on a pseudo-conductive high-electron mobility transistor (PC-HEMT). In some embodiments, the transistor comprises free-standing membranes, on which a multilayer hetero-junction structure is deposited. This hetero-junction structure may comprise at least two layers, a buffer layer and a barrier layer, which are grown from III-V single-crystalline or polycrystalline semiconductor materials. The free-standing membranes are free-standing columns of substrate composed of sapphire, silicon, silicon carbide, gallium nitride or aluminium nitride, having thickness of 0.5-2 μm, for creating mass-loading effect and allowing a pressure sensing mode of the sensor.

A conducting channel comprising a two-dimensional electron gas (2DEG), in case of two-layers configuration, or a two-dimensional hole gas (2DHG), in case of three-layers configuration, is formed at the interface between the buffer and barrier layers and provides electron or hole current in the system between source and drain electrodes. The source and drain, either ohmic or capacitively-coupled (non-ohmic) contacts are connected to the formed 2DEG/2DHG channel and to electrical metallizations, the latter are placed on top of the transistor and connect it to the sensor system. An optional dielectric layer is deposited on top of the hetero-junction structure. The open gate area of the transistor is formed between the source and drain areas as a result of recessing or growing of the top layer to a specific thickness.

If the source and drain contacts are non-ohmic (capacitively-coupled), in order to electrically contact the 2DEG/2DHG channel underneath, which is about 5-20 nm below metallizations, the AC-frequency regime is used. The capacitive coupling of the non-ohmic metal contacts with the 2DEG/2DHG channel is normally induced at the frequency higher than 30 kHz. In the case of non-ohmic contacts, the DC readout cannot be carried out. Instead, the AC readout or impedance measurements of the electric current flowing through the 2DEG/2DHG-channel are performed.

In some embodiments, the significant features of the PC-HEMT structure are that:
(i) the thickness of the top layer in the open gate area between the source and drain contacts is 5-9 nm, preferably 6-7 nm, more preferably 6.3 nm, and that corresponds to the pseudo-conducting current range between normally-on and normally-off operation mode of the transistor, (ii) the surface of the top layer within the open gate area between the source and drain contacts has a roughness of about 0.2 nm or less, preferably 0.1 nm or less, more preferably 0.05 nm, and
(iii) the non-ohmic source and drain contacts for the capacitive coupling with the conductive 2DEG/2DHG channel optionally replace the ohmic contacts.

In some embodiments, the PC-HEMT multilayer hetero-junction structure of the present application is grown from any available III-V single-crystalline or polycrystalline semiconductor materials, such as GaN/AlGaN, GaN/AlN, GaN/InN, GaN/InAlGaN, GaAs/AlGaAs GaN/InAlN, InN/InAlN, and $LaAlO_3/SrTiO_3$. In case of the GaN/AlGaN PC-HEMT, it has been surprisingly found that in the open gate area of the PC-HEMT, the thickness of the top layer that corresponds to the pseudo-conducting current range between normally-on and normally-off operation mode of the PC-HEMT, is about 6-7 nm.

In a particular embodiment, the hetero-junction structure may be a three-layer structure consisting of two buffer layers and one barrier layer squeezed between said buffer layers like in a sandwich. This may lead to formation of the two-dimensional hole gas (2DHG) in the top buffer layer above the barrier layer which results in reversing polarity of the transistor.

In some embodiments, the present application provides the PC-HEMT-based microelectronic sensor for use in hypersensitive microphones.

Various embodiments may allow various benefits, and may be used in conjunction with various applications. The details of one or more embodiments are set forth in the accompanying figures and the description below. Other features, objects and advantages of the described techniques will be apparent from the description and drawings and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Disclosed embodiments will be understood and appreciated more fully from the following detailed description taken in conjunction with the appended figures. The drawings included and described herein are schematic and are not limiting the scope of the disclosure. It is also noted that in the drawings, the size of some elements may be exaggerated and, therefore, not drawn to scale for illustrative purposes. The dimensions and the relative dimensions do not necessarily correspond to actual reductions to practice of the disclosure.

FIG. 2a schematically shows a cross-sectional view of the PC-HEMT of an embodiment with free-standing membranes.

FIG. 2b illustrates a situation when the external pressure (mass effect) is applied on the sensor incorporating the PC-HEMT of FIG. 11a, and transferred into a changed internal strain caused by bending.

FIG. 6a schematically shows the formation of the 2DEG and 2DHG conducting channels in the Ga-face three-layer GaN/AlGaN/GaN PC-HEMT structure.

FIG. 6b schematically shows the formation of the 2DEG and 2DHG conducting channels in the N-face three-layer GaN/AlGaN/GaN PC-HEMT structure.

FIG. 8c illustrates a top view of the PC-HEMT-based microphone of embodiments with a recessed AlGaN barrier layer, placed on free-standing membranes.

FIGS. 11a-11b show an exemplary stethoscope design.

FIGS. 14a-14c show the expanded part of the phonocardiogram of FIG. 13 for 6-7 seconds in a zoom-in sequence.

DETAILED DESCRIPTION

Figure 1A:
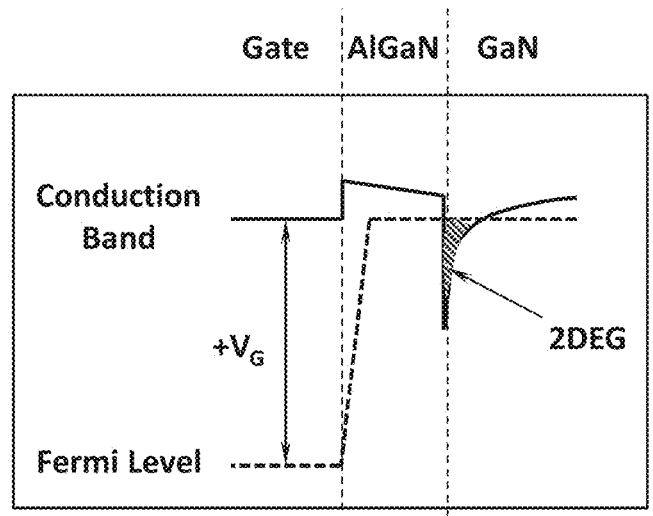
FIG. 1(a) the positive gate potential ($+V_G$), much higher than the threshold voltage ($V_T$), FIG. 1(b) 0V gate potential, and FIG. 1(c) negative gate potential ($-V_G$) below the threshold voltage ($V_T$).
Figure 1B:
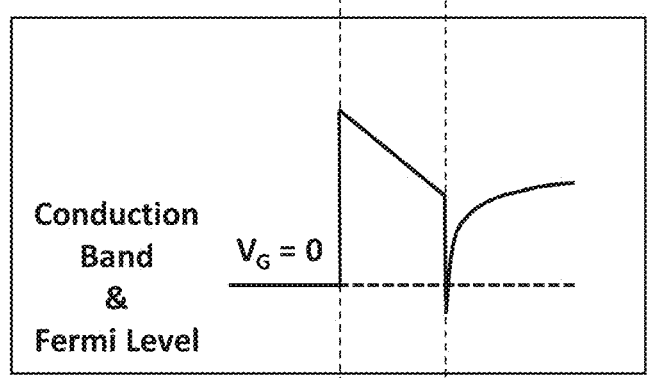
FIG. 1 schematically shows the quantum well at three different biasing conditions.
Figure 1C:
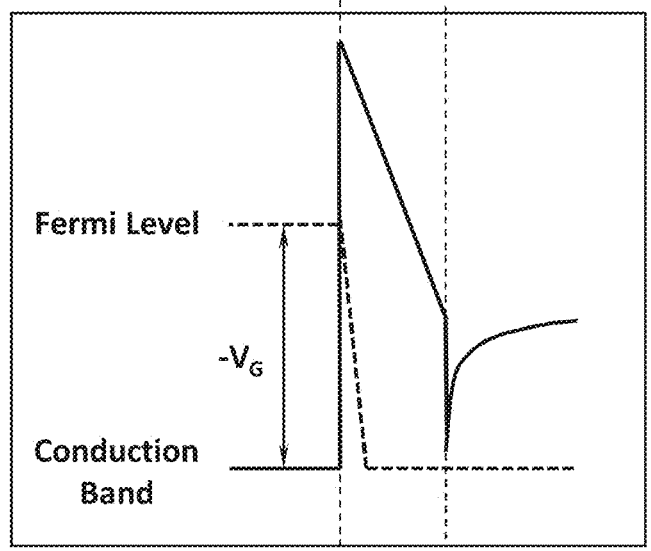

In the following description, various aspects of the present application will be described. For purposes of explanation, specific configurations and details are set forth in order to provide a thorough understanding of the present application. However, it will also be apparent to one skilled in the art that the present application may be practiced without the specific details presented herein. Furthermore, well-known features may be omitted or simplified in order not to obscure the present application.

The term "comprising", used in the claims, should not be interpreted as being restricted to the means listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising x and z" should not be limited to devices consisting only of components x and z. As used herein, the term "about" means there is a 10% tolerance of the mentioned or claimed value. As used herein, the term "and/or" includes any and all combinations of one or more of the associated listed items. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached to", "connected to", "coupled with", "contacting", etc., another element, it can be directly on, attached to, connected to, coupled with or contacting the other element or intervening elements may also be present. In contrast, when an element is referred to as being, for example, "directly on", "directly attached to", "directly connected to", "directly coupled" with or "directly contacting" another element, there are no intervening elements present. It will also be appreciated by those of skill in the art that references to a structure or feature that is disposed "adjacent" another feature may have portions that overlap or underlie the adjacent feature.

The sensor of an embodiment is based essentially on the open-gate pseudo-conductive high-electron mobility transistor (PC-HEMT) disclosed in the patent application U.S. Ser. No. 15/067,093 and U.S. Ser. No. 15/157,285. The phenomenon of the pseudo-conductive current described in those applications makes the PC-HEMT-based sensor of an embodiment extremely sensitive.

FIG. 2a shows a cross-sectional view of an open-gate pseudo-conductive high-electron mobility transistor (PC-HEMT) of an embodiment of the present application comprising:

a multilayer hetero-junction structure made of III-V single-crystalline or polycrystalline semiconductor materials, said structure comprising at least one buffer layer (11) and at least one barrier layer (12), said layers being stacked alternately, and said structure being placed on free-standing membranes (23);

a conducting channel (13) comprising a two-dimensional electron gas (2DEG) or a two-dimensional hole gas (2DHG), formed at the interface between said buffer layer (11) and said barrier layer (12) and providing electron or hole current in said transistor between source and drain contacts (15);

the source and drain contacts (15) connected to said 2DEG or 2DHG conducting channel and to electrical metallizations (14) for connecting said transistor to an electric circuit; and an open gate area (17) between said source and drain non-ohmic contacts;

wherein:

(i) the thickness of the top barrier layer (12) in the open gate area (17) is 5-9 nm which corresponds to the pseudo-conducting current range between normally-on and normally-off operation mode of the transistor, and (ii) the surface of the top barrier layer (12) has a roughness of about 0.2 nm or less.

The 2DEG channel (13) formed near the interface between the buffer layer (11) and the barrier layer (12) serves as a main sensitive element of the transistor reacting to a surface charge and potential. The 2DEG channel (13) is configured to interact with very small variations in surface or proximal charge or changes of electrical field on the barrier layer/liquid-air or barrier layer/metal/liquid-air interfaces interacting with the donor-like surface trap states of the barrier layer. This will be defined and discussed below in detail.

The term "2DEG" mentioned in the following description and claims should not be understood or interpreted as being restricted to the two-dimensional electron gas. As stated above and will be explained later in this application, the two-dimensional hole gas may also be a possible current carrier in a specific hetero-junction structure. Therefore, the term "2DEG" may be equally replaced with the term "2DHG" without reference to any specific PC-HEMT configuration.

The PC-HEMT shown in FIG. 2a may be used as a "pressure-sensitive" sensor, which is capable of measuring very small pressures created by sound waves. It uses the free-standing membranes for creating a mass-loading effect which makes it possible to increase sensitivity and selectivity of the sensors via adding mechanical stress (mass-loading effect) as an additional parameter of the PC-HEMT-based sensor. The free-standing membranes (23) are very flexible free-standing columns of substrate composed of sapphire, silicon, silicon carbide, gallium nitride or aluminium nitride, preferably gallium nitride, having thickness of 0.5-2 μm. The free-standing substrate membranes are very sensitive to any tensile, compressive or mechanical stress changes on the surface of the multilayer heterojunction structure. This results in a mass loading effect, which will be discussed below.

In general, mechanical sensors, much like pressure sensors, are based on the measurement of the externally induced strain in the heterostructures. The pyroelectric properties of group-III-nitrides, such as gallium nitride (GaN), allow two mechanisms for strain transduction: piezoelectric and piezoresistive. The direct piezoelectric effect is used for dynamical pressure sensing. For measurements of static pressure, such sensors are not suitable due to some leakage of electric charges under the constant conditions. For static operation, the piezoresistive transduction is more preferable.

Piezoresistive sensors using wide band gap materials have been previously employed using hexagonal silicon carbide bulk materials for high temperature operation. Piezoresistivity of GaN and AlGaN structures is comparable to silicon carbide. However, piezoresistivity can be further amplified by HEMT structure, as taught by Eickhoff et al (2001). For piezoresistive strain sensing at relatively lower pressures (or pressure differences), such as those created by sound waves, diaphragm or membranes should be used, where the external pressure is transferred into a changed internal strain caused by bending, as shown in FIG. 2b. The resulting change in polarization alters the electron or hole current in the 2DEG or 2DHG channel (13) which is measured.

Eickhoff et al (2001) conducted the first experiments on AlGaN/GaN heterostructures where the 2DEG channel confined between the upper GaN and AlGaN barrier layer and demonstrated the linear dependence of the 2DEG channel resistivity on the applied strain. Moreover a direct comparison to cubic SiC and a single AlGaN layer clearly demonstrated the superior piezoresistive properties of the latter. From these results, it is clear that the interaction of piezoelectric and piezoresistive properties improves the sensitivity of pressure sensors by using GaN/AlGaN heterostructures confined with the 2DEG channel.

The sensor configuration shown in FIG. 2a involves piezoelectrically coupled, charge and mass sensitive, free-standing GaN membranes, which are prepared, for example, according to U.S. Pat. No. 8,313,968, and offer an elegant and effective solution to achieve both downscaling and an integrated all-electrical low-power sensing-actuation. As mentioned above, GaN exhibits both, piezo- and pyro-electrical properties, which can be functionally combined. Whereas the piezoelectricity enables realisation of an integrated coupling mechanism, the 2DEG additionally delivers a pronounced sensitivity to mechanical stress and charge, which allows the sensor to use the pyroelectric effects. The dynamic change in 2DEG conductivity is also caused by a change in piezoelectric polarisation.

The PC-HEMT, which is shown on FIG. 2a, may further comprise a dielectric layer of approximately 1-10 nm thickness, which is used for device passivation. This dielectric layer is deposited on top of the barrier layer (12). In one embodiment, the dielectric layer is made, for example, of SiO—SiN—SiO ("ONO") stack of 100-100-100 nm thickness or SiN—SiO—SiN ("NON") stack having the same thicknesses. This dielectric layer is deposited on top of the barrier layer by a method of plasma-enhanced chemical vapour deposition (PECVD), which is a stress-free deposition technique.

"Capacitive coupling" is defined as an energy transfer within the same electric circuit or between different electric circuits by means of displacement currents induced by existing electric fields between circuit/s nodes. In general, ohmic contacts are the contacts that follow Ohm's law, meaning that the current flowing through them is directly proportional to the voltage. Non-ohmic contacts however do not follow the same linear relationship of the Ohm's law. In other words, electric current passing through non-ohmic contacts is not linearly proportional to voltage. Instead, it gives a steep curve with an increasing gradient, since the resistance in that case increases as the electric current increases, resulting in increase of the voltage across non-ohmic contacts. This is because electrons carry more energy, and when they collide with atoms in the conductive channel, they transfer more energy creating new high-energy vibrational states, thereby increasing resistance and temperature.

When electrical metallizations are placed over single-crystalline or polycrystalline semiconductor material, the "Schottky contact" or "Schottky barrier contact" between the metal and the semiconductor occurs. Energy of this contact is covered by the Schottky-Mott rule, which predicts the energy barrier between a metal and a semiconductor to be proportional to the difference of the metal-vacuum work function and the semiconductor-vacuum electron affinity. However, this is an ideal theoretical behaviour, while in reality most interfaces between a metal and a semiconductor follow this rule only to some degree. The boundary of a semiconductor crystal abrupt by a metal creates new electron states within its band gap. These new electron states induced by a metal and their occupation push the centre of the band gap to the Fermi level. This phenomenon of shifting the centre of the band gap to the Fermi level as a result of a metal-semiconductor contact is defined as "Fermi level pinning", which differs from one semiconductor to another. If the Fermi level is energetically far from the band edge, the Schottky contact would preferably be formed. However, if the Fermi level is close to the band edge, an ohmic contact would preferably be formed. The Schottky barrier contact is a rectifying non-ohmic contact, which in reality is almost independent of the semiconductor or metal work functions.

Thus, a non-ohmic contact allows electric current to flow only in one direction with a non-linear current-voltage curve that looks like that of a diode. On the contrary, an ohmic contact allows electric current to flow in both directions roughly equally within normal device operation range, with an almost linear current-voltage relationship that comes close to that of a resistor (hence, "ohmic").

Figure 3:
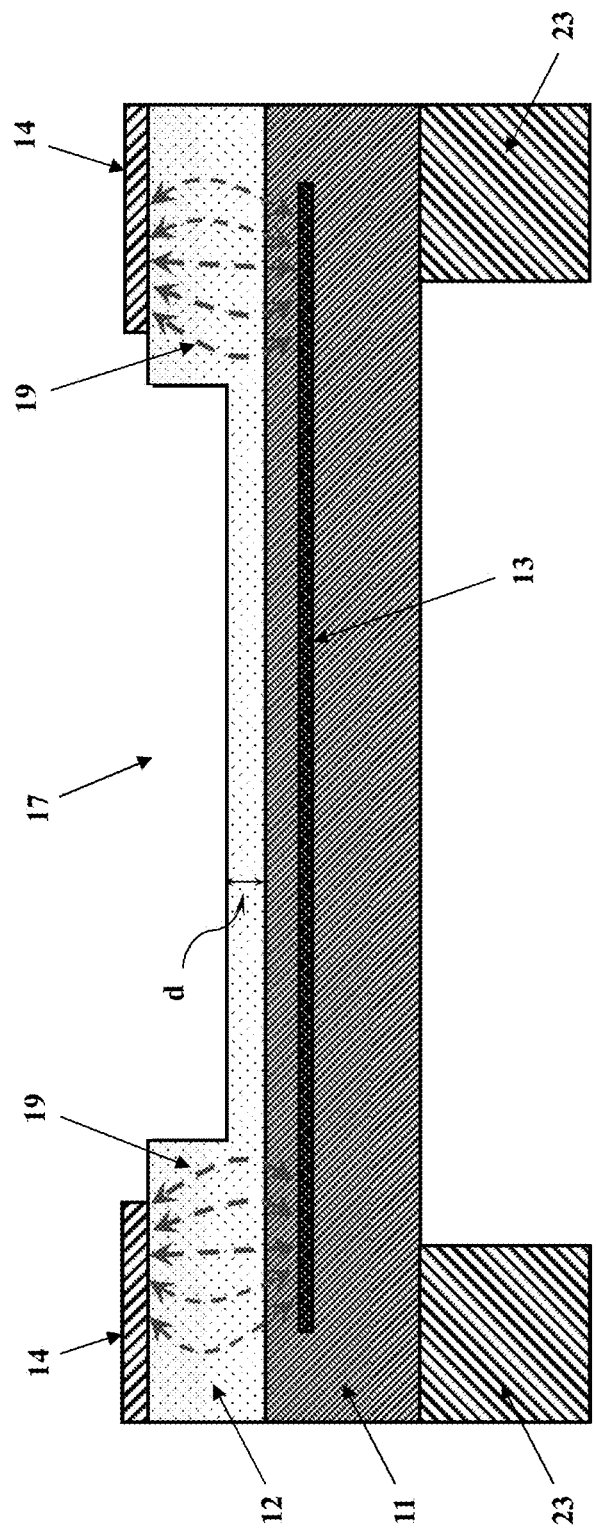
FIG. 3 schematically shows a cross-sectional view of the PC-HEMT of an embodiment having non-ohmic (capacitively-coupled) contacts.

FIG. 3 illustrates the situation when an electrical connection of the transistor to the 2DEG channel is realised via the capacitive coupling to electrical metallizations through a Schottky barrier contact. This coupling becomes possible only if sufficiently high AC frequency, higher than 30 kHz, is applied to the metallizations. The electrical metallizations capacitively coupled to the 2DEG channel utilise the known phenomenon of energy transfer by displacement currents, which are induced by existing electrical fields between the electrical metallizations and the 2DEG conducting channel operated in the AC frequency mode through the Schottky contact, as explained above.

Another option would be the use of the photoeffect that may also induce an electric current in the 2DEG channel. In order to couple the light excitation with the electronic effects in the conductive 2DEG channel, a photoeffect in a silicon layer should be created. Regarding the direct photoeffect, it is well known that light can only be absorbed when the energy of the absorbed photon (E=hν) is large enough for an electron to be excited into the valence band. In that case, E is the photon energy, h is Planck's constant and ν is the frequency of the photon. The frequency is coupled to the wavelength λ of light by the constant speed of light c=λν. Typically the bandgap of silicon at room temperature is 1.12.eV, which means that silicon becomes transparent for wavelength larger than 1240 nm, which is the near infrared range.

For smaller wavelength (i.e. larger energy of the photons), electron/hole pairs are generated leading to a photocurrent. In the fully-depleted, intrinsically doped silicon structures, this results in a higher charge carrier density and consequently, higher sensitivity. For these structures, light is adsorbed in the whole visible range making such devices ideal photodetectors. The mechanism that allows the silicon semiconductor to become photosensitive to irradiation with light has already been described in literature. In the direct photoeffect, it can be tuned by the size, crystalline direction and surface termination. These effects originate from two-dimensional quantum confinement of electrons in the nano-sized 2DEG structure.

Although irradiation of the silicon structure with light of larger wavelengths with photon energies below the bandgap does not have enough energy to excite carriers from the valence to the conduction band in bulk silicon, the electron/hole pairs can also be generated between the valence band and surface states, and the donor-like surface trap states can still be formed (see the definition and explanation of the surface trap states below). The electrons actually deplete the holes trapped at the surface and hence, modulate the gate field. The photogenerated holes are confined to the centre of the silicon structure by the gate field, where they increase the conduction of the 2DEG channel, because of the band bending. The holes increase the channel conductivity for a certain lifetime until they are trapped (recaptured) at the surface. The gain of the transistor can be extremely huge if this re-trapping lifetime is much longer than the holes transit time.

If the source and drain contacts are non-ohmic (capacitively-coupled), as in the configuration shown in FIG. 3, in order to electrically contact the 2DEG channel underneath, which is about 5-20 nm below metallizations, the AC frequency regime is used. The capacitive coupling of the non-ohmic metal contacts with the 2DEG channel is normally induced at the frequency higher than 30 kHz. In the case of non-ohmic contacts, the DC readout cannot be performed. Instead, the AC readout or impedance measurements of the electric current flowing through the 2DEG channel are carried out.

In some embodiments, the significant features of the PC-HEMT structure are that:
(i) the non-ohmic source and drain contacts for the capacitive coupling with the conductive 2DEG channel are used,
(ii) the thickness of the barrier layer in the open gate area is 5-9 nm which corresponds to the pseudo-conducting current range between normally-on and normally-off operation mode of the transistor, and
(iii) the surface of the barrier layer has a roughness of about 0.2 nm or less.

In a specific embodiment, the III-V semiconductor materials are selected from the pairs GaN/AlGaN, GaN/AlN, GaN/InN, GaN/InAlN, InN/InAlN, GaN/InAlGaN, GaAs/AlGaAs and $LaAlO_3/SrTiO_3$.

In another embodiment, electrical metallizations (14) connect the transistor to an electric circuit and allow electric current to flow between the non-ohmic contacts, which are capacitively coupled to the conducting 2DEG channel (13) via displacement currents (19). The electrical metallizations (14) are made of metal stacks, such as Cr/Au, Ti/Au, Ti/W, Cr/Al and Ti/Al. The Cr or Ti layers of the metal stack is, for example, of about 5-10 nm thickness, while the second metal layer, such as Au, W and Al, is of about 100-400 nm thickness. The actual metallizations (14) are chosen according to the established technology and assembly line at a particular clean room fabrication facility.

In yet further embodiment, the barrier layer (12) may be either recessed or grown as a thin layer between the non-ohmic source and drain contacts, thereby forming an open gate area. "Open gate area" of the PC-HEMT is defined as an area between the source and drain non-ohmic contacts of the transistor which is directly exposed to a conductive medium, such as liquid or gas capable of conducting current. The specific thickness of the barrier layer (12) in the open gate area is achieved by either dry etching the semiconductor material of the layer (12), i.e. recessing layer in the open gate area with the etching rate of 1 nm per 1-2 min in a controllable process, or coating the buffer layer (11) in the open gate area with an ultrathin layer of the III-V semiconductor material. In order to increase the charge sensitivity of the transistor, the surface of the recessed ultrathin barrier layer is post-treated with plasma (chloride) epi-etch process. Consequently, the natively passivated surface is activated by the plasma etch to create an uncompensated (ionised) surface energy bonds or states, which are neutralized after the metal-organic chemical vapour deposition (MOCVD) growing.

Figure 4:
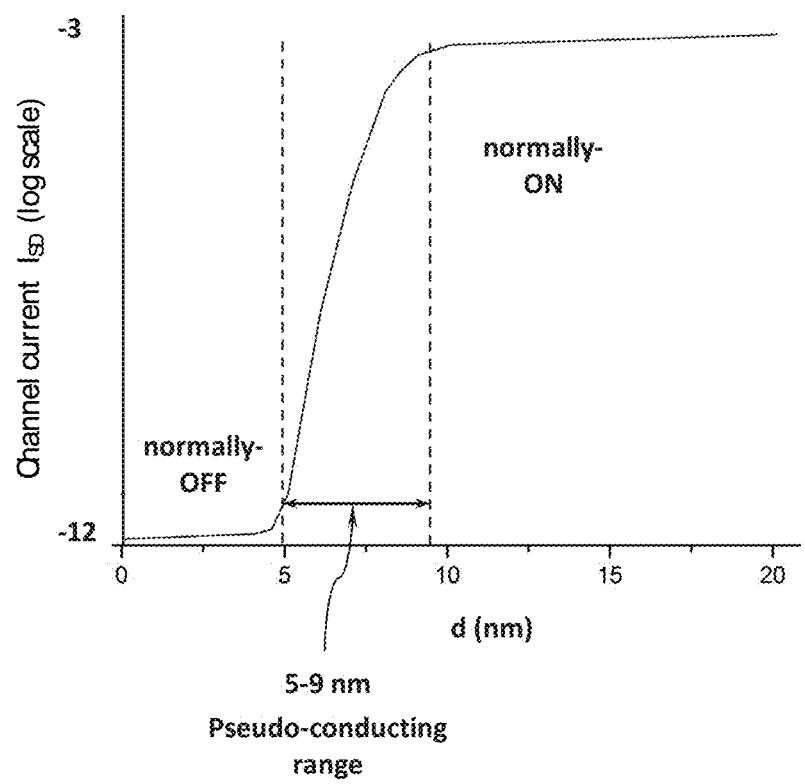
FIG. 4 schematically shows the dependence of the source-drain current (a charge carrier density) induced inside the 2DEG channel of a GaN/AlGaN HEMT on the thickness of the AlGaN barrier layer recessed in the open gate area.

FIG. 4 shows the dependence of the source-drain current (a charge carrier density) on the barrier layer thickness recessed in the open gate area. As seen from the plot, the HEMTs that have a thickness of the barrier layer in the open gate area larger than about 9 nm are normally-on devices. In such devices, the inherent macroscopic spontaneous polarisation effects present in the ionic bonds of III-V materials, a thin sheet of charges is induced at the top and bottom of the interfaces of the barrier layer, thereby forming the 2DEG layer. In other words, once a high electric field is induced in the barrier layer, the surface donor states at the top interface start donating electrons to form the 2DEG channel at the proximity of the hetero-junction interface without the application of a gate bias. These HEMTs are therefore normally-on devices. On the other hand, the HEMTs that have a thickness of the barrier layer in the open gate area lower than about 5 nm act as normally-off devices.

The barrier layer recessed or grown in the open gate area to 5-9 nm is optimised for significantly enhancing sensitivity of the PC-HEMT sensor. This specific thickness of the barrier layer in the open gate area corresponds to the "pseudo-conducting" current range between normally-on and normally-off operation modes of the transistor and requires further explanation.

"Pseudo-contacting" current range of the HEMT is defined as an operation range of the HEMT between its normally-on and normally-off operation modes. "Trap states" are states in the band-gap of a semiconductor which trap a carrier until it recombines. "Surface states" are states caused by surface reconstruction of the local crystal due to surface tension caused by some crystal defects, dislocations, or the presence of impurities. Such surface reconstruction often creates "surface trap states" corresponding to a surface recombination velocity. Classification of the surface trap states depends on the relative position of their energy level inside the band gap. The surface trap states with energy above the Fermi level are acceptor-like, attaining negative charge when occupied. However, the surface trap states with energy below the Fermi level are donor-like, positively charged when empty and neutral when occupied. These donor-like surface trap states are considered to be the source of electrons in the formation of the 2DEG channel. They may possess a wide distribution of ionization energies within the band gap and are caused by redox reactions, dangling bonds and vacancies in the surface layer. A balance always exists between the 2DEG channel density and the number of ionised surface donors which is governed by charge neutrality and continuity of the electric field at the interfaces.

Thus, the donor-like surface traps at the surface of the barrier layer of the HEMT are one of the most important sources of the 2DEG in the channel. However, this only applies for a specific barrier layer thickness. In a relatively thin barrier layer, the surface trap state is below the Fermi level. However, as the barrier layer thickness increases, the energy of the surface trap state approaches the Fermi energy until it coincides with it. The thickness of the barrier layer corresponding to such situation is defined as "critical". At this point, electrons filling the surface trap state are pulled to the channel by the strong polarisation-induced electric field found in the barrier to form the 2DEG instantly.

If the surface trap states are completely depleted, further increase in the barrier layer thickness will not increase the 2DEG density. Actually, if the 2DEG channel layer fails to stretch the barrier layer, the later will simply relax. Upon relaxation of the barrier layer, crystal defects are created at the interface between the buffer and barrier layers, and the piezoelectric polarisation disappears causing deterioration in the 2DEG density.

Figure 5:
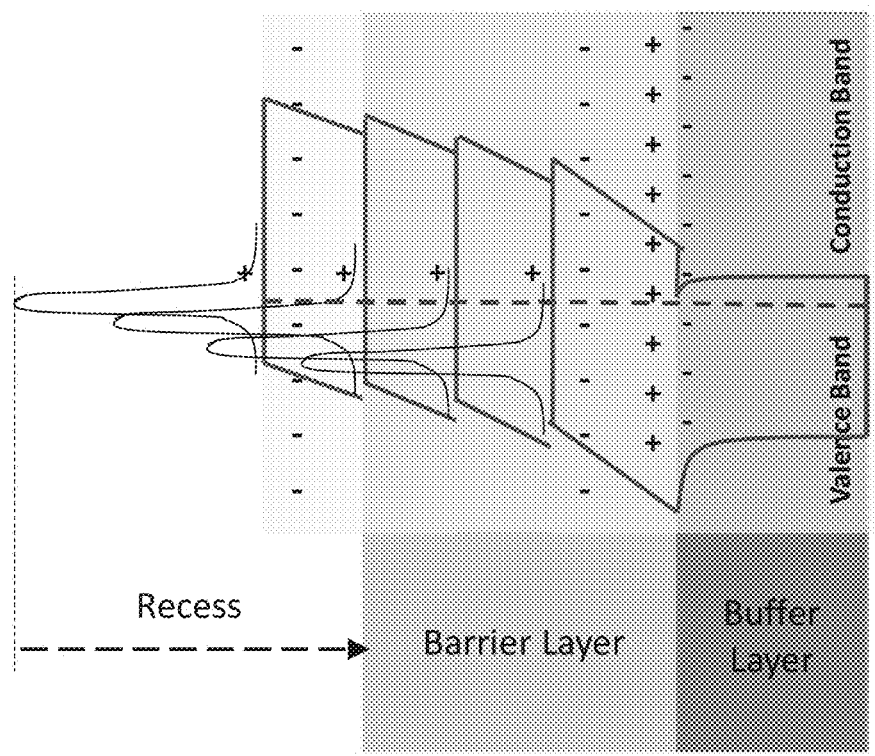
FIG. 5 illustrates a theory behind the 2DEG formation (charge neutrality combined with the lowest energy level) at the conduction band discontinuity.

In order to illustrate the above phenomenon of pseudo-conducting current, reference is now made to the following figures. As mentioned above, FIG. 4 shows the dependence of the source-drain current (a charge carrier density) on the recessed AlGaN barrier layer thickness. An energy equilibrium between the donor surface trap states and the AlGaN tunnel barrier leads to the 2DEG formation (charge neutrality combined with the lowest energy level) at the conduction band discontinuity. As explained above, decrease in the thickness of the barrier layer results in increase of the energy barrier. As a result, the ionisable donor-like surface trap states, which are responsible for electron tunneling from the surface to 2DEG, drift below the Fermi level, thereby minimizing the electron supply to the 2DEG channel. This theoretical situation is illustrated in FIG. 5. Therefore, the recess of the AlGaN layer from 9 nm to 5 nm leads to extremely huge drop in the 2DEG conductivity for six orders of magnitude.

Thus, the mechanism of the 2DEG depletion based on recessing the barrier layer is strongly dependent on the donor-like surface trap states (or total surface charge). As the thickness of the barrier layer decreases, less additional external charge is needed to apply to the barrier layer surface in order to deplete the 2DEG channel. There is a critical (smallest) barrier thickness, when the 2DEG channel is mostly depleted but still highly conductive due to a combination of the energy barrier and the donor surface trap states energy. At this critical thickness, even the smallest energy shift at the surface via any external influence, such as surface reaction, charging etc., leads immediately to very strong 2DEG depletion. As a result, the surface of the barrier layer at this critical thickness is extremely sensitive to any smallest change in the electrical field of the surroundings.

In view of the above, recess of the gate area of the barrier layer from 9 nm down to 5 nm significantly reduced the 2DEG density, brought the transistor to the "near threshold" operation and resulted in highly increased surface charge sensitivity. The specific 5-9 nm thickness of the barrier layer responsible for the pseudo-conducting behaviour of the transistor gives the sensor an incredible sensitivity. So, when it comes into a contact with an ionic fluid or body skin, it opens up the gate to be able to do the ultrasensitive sensing.

In addition to the recessed or grown barrier layer thickness, roughness of the barrier layer surface is another very important parameter that has not been previously disclosed. It has been surprisingly found that that the roughness of the barrier layer surface (in the open gate sensitive area) below 0.2 nm prevents scattering of the donor-like surface trap states.

In a further aspect, the hetero-junction structure may be a three-layer structure consisting of two buffer layers and one barrier layer squeezed between said buffer layers like in a sandwich, wherein the top layer is a buffer layer. This may lead to formation of the two-dimensional hole gas (2DHG) in the top buffer layer above the barrier layer which results in reversing polarity of the transistor compared to the two-layer structure discussed above.

In general, polarity of III-V nitride semiconductor materials strongly affects the performance of the transistors based on these semiconductors. The quality of the wurtzite GaN materials can be varied by their polarity, because both the incorporation of impurities and the formation of defects are related to the growth mechanism, which in turn depends on surface polarity. The occurrence of the 2DEG/2DHG and the optical properties of the hetero-junction structures of nitride-based materials are influenced by the internal field effects caused by spontaneous and piezo-electric polarizations. Devices in all of the III-V nitride materials are fabricated on polar {0001} surfaces. Consequently, their characteristics depend on whether the GaN layers exhibit Ga-face positive polarity or N-face negative polarity. In other words, as a result of the wurtzite GaN materials polarity, any GaN layer has two surfaces with different polarities, a Ga-polar surface and an N-polar surface. A Ga-polar surface is defined herein as a surface terminating on a layer of Ga atoms, each of which has one unoccupied bond normal to the surface. Each surface Ga atom is bonded to three N atoms in the direction away from the surface. In contrast, an N-polar surface is defined as a surface terminating on a layer of N atoms, each of which has one unoccupied bond normal to the surface. Each surface N atom is also bonded to three Ga atoms in the direction away from the surface. Thus, the N-face polarity structures have the reverse polarity to the Ga-face polarity structures.

As described above for the two-layer heterojunction structure, the barrier layer is always placed on top of the buffer layer. The layer which is therefore recessed is the barrier layer, specifically the AlGaN layer. As a result, since the 2DEG is used as the conducting channel and this conducting channel is located slightly below the barrier layer (in a thicker region of the GaN buffer layer), the hetero-junction structure is grown along the {0001}-direction or, in other words, with the Ga-face polarity. However, as explained above, the physical mechanism that leads to the formation of the 2DEG is a polarisation discontinuity at the AlGaN/GaN interface, reflected by the formation of the polarisation-induced fixed interface charges that attract free carriers to form a two-dimensional carrier gas. It is a positive polarisation charge at the AlGaN/GaN interface that attracts electrons to form 2DEG in the GaN layer slightly below this interface.

As noted above, polarity of the interface charges depends on the crystal lattice orientation of the hetero-junction structure, i.e. Ga-face versus N-face polarity, and the position of the respective AlGaN/GaN interface in the hetero-junction structure (above or below the interface). Therefore, different types of the accumulated carriers can be present in the hetero-junction structure of the embodiments.

In case of the three-layer hetero-junction structure, there are four possible configurations:

Ga-Face Polarity

1) The Ga-face polarity is characterised by the 2DEG formation in the GaN layer below the AlGaN barrier layer. This is actually the same two-layer configuration as described above, but with addition of the top GaN layer. In this configuration, the AlGaN barrier layer and two GaN buffer layers must be nominally undoped or n-type doped.

2) In another Ga-face configuration shown in FIG. 6a, in order to form the conducting channel comprising a two-dimensional hole gas (2DHG) in the top GaN layer above the AlGaN barrier layer in the configuration, the AlGaN barrier layer should be p-type doped (for example, with Mg or Be as an acceptor) and the GaN buffer layer should be also p-type doped with Mg, Be or intrinsic.

N-Face Polarity

3) The N-face polarity is characterised by the 2DEG formation in the top GaN layer above the AlGaN barrier layer, as shown in FIG. 6b. In this case, the AlGaN barrier layer and two GaN buffer layers must be nominally undoped or n-type doped.

4) The last configuration assumes that the 2DHG conducting channel is formed in the buffer GaN layer below the AlGaN barrier layer. The top GaN layer may be present (three-layer structure) or not (two-layer structure) in this case. The AlGaN barrier layer must be p-type doped (for example with Mg or Be as an acceptor) and the bottom GaN layer should be also p-type doped with Mg, Be or intrinsic.

Thus, there are four hetero-junction three-layer structures implemented in the transistor of the embodiments, based on the above configurations:

A. Ga-Face GaN/AlGaN/GaN heterostructure with the 2DEG formed in the GaN buffer layer below the AlGaN barrier layer. In this case, the top GaN layer may be omitted to obtain the two-layer structure. For the three-layer structure, the top GaN layer must be recessed to 1-9 nm thickness in the open gate area or grown with this low thickness, with the roughness below 0.2 nm, and the thickness of the AlGaN barrier can be adjusted properly during growth.

B. Ga-Face GaN/AlGaN/GaN heterostructure with the 2DHG conducting channel formed in the top GaN layer above the AlGaN barrier layer. The top GaN layer must be recessed to 5-9 nm thickness in the open gate area with the roughness below 0.2 nm, and the thickness of the AlGaN barrier layer can be adjusted properly. P-type doping concentrations of the GaN layer and AlGaN barrier have to be adjusted; the 2DHG has to be contacted (in the ideal case by ohmic contacts).

C. N-Face GaN/AlGaN/GaN heterostructure with the 2DEG in the top GaN layer above the AlGaN barrier layer. The top GaN layer must be recessed to 5-9 nm thickness in the open gate area with the roughness below 0.2 nm. Thickness of the AlGaN barrier can be adjusted during growth. N-type doping levels of the GaN buffer layer and the AlGaN barrier layer must be adjusted; the 2DEG has to be contacted (in the ideal case by ohmic contacts).

N-Face GaN/AlGaN/GaN heterostructure with the 2DHG in the GaN buffer layer below the AlGaN barrier layer. In this case, the top GaN layer may be omitted to obtain the two-layer structure. In both, the two-layer and three-layer configurations, the top GaN layer must be recessed to 1-9 nm thickness in the open gate area with the roughness below 0.2 nm, and the thickness of the AlGaN barrier can be adjusted properly.

Figure 7:
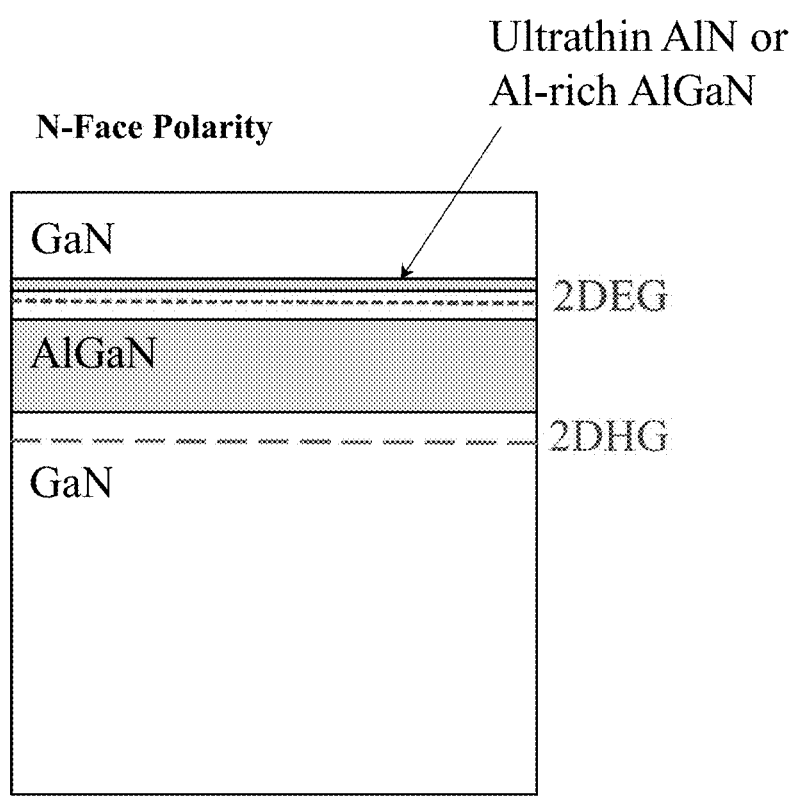
FIG. 7 schematically shows the formation of the 2DEG conducting channel in the N-face three-layer GaN/AlGaN/GaN PC-HEMT structure with an ultrathin Al(GaN)N layer for improved confinement.

In all the above structures, the deposition of a dielectric layer on top might be beneficial or even necessary to obtain a better confinement (as in case of the N-face structures). As shown in FIG. 7, for the above "C" structure, it may be even more beneficial to include an ultrathin (about 1 nm) AlN or AlGaN barrier layer with high Al-content on top of the 2DEG channel to improve the confinement.

The preferable structures of the embodiments are structures "B" and "C". In the structure "B", the 2DHG conducting channel formed in the top GaN layer, which has a higher chemical stability (particularly towards surface oxidation) than the AlGaN layer. Concerning the structure "C", the 2DEG conducting channel might be closer to the surface. Therefore, the electron mobility might be lower than in the 2DEG structure with the Ga-face polarity. In general, the polarity of the heterostructure can be adjusted by the choice of the substrate (e.g. C-face SiC) or by the growth conditions.

Thus, combination of these two features, 5-9 nm thickness of the barrier layer and strongly reduced roughness of its surface, make the PC-HEMT an incredibly strong functional amplifier.

Figure 8A:
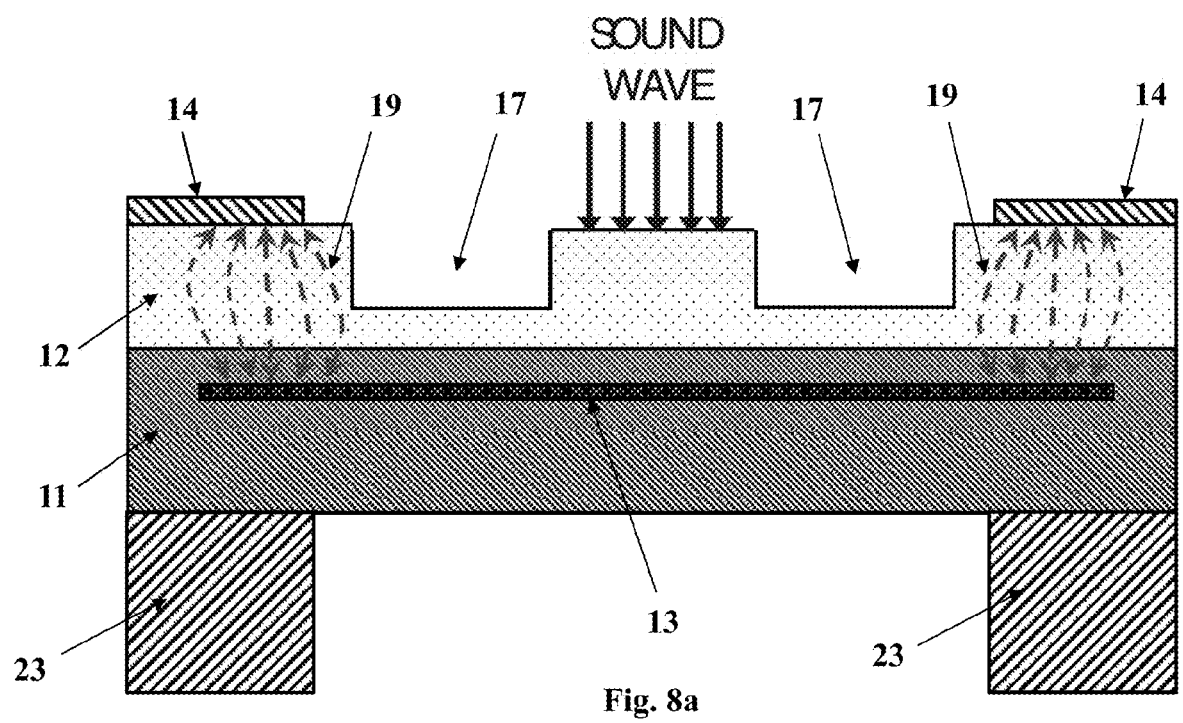
FIGS. 8a-8b schematically shows a cross-sectional view (XZ) (a) and a top view (XY) (b) of the PC-HEMT of embodiments with a recessed AlGaN barrier layer, placed on free-standing membranes.
Figure 8B:
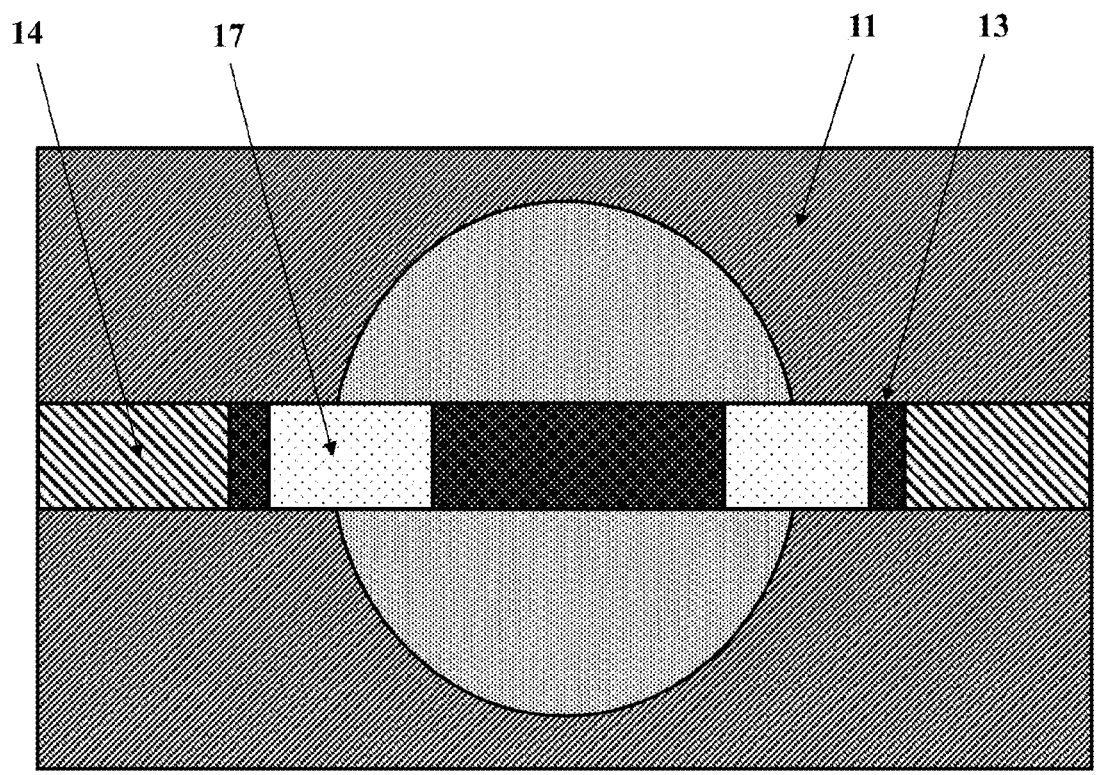

In a further aspect of the present application, FIGS. 8a-8b shows a cross-sectional view (XZ) (a) and a top view (XY) (b) of the PC-HEMT of embodiments with a recessed AlGaN barrier layer, comprising:

a multilayer hetero-junction structure made of III-V single-crystalline or polycrystalline semiconductor materials, said structure comprising at least one buffer layer (11) and at least one barrier layer (12), said layers being stacked alternately, and said structure being placed on free-standing membranes (23);

a conducting channel (13) comprising a two-dimensional electron gas (2DEG) or a two-dimensional hole gas (2DHG), formed at the interface between said buffer layer (11) and said barrier layer (12) and providing electron or hole current in said transistor between source and drain non-ohmic contacts; and electrical metallizations (14) capacitively-coupled to said 2DEG or 2DHG channel (13) for inducing displacement currents (19), thereby creating non-ohmic source and drain contacts connecting said transistor to an electric circuit; and an open gate area (17) between said source and drain non-ohmic contacts;

wherein:
(i) the thickness of the top barrier layer (12) in the open gate area (17) is 5-9 nm which corresponds to the pseudo-conducting current range between normally-on and normally-off operation mode of the transistor, and
(ii) the surface of the top barrier layer (12) has a roughness of about 0.2 nm or less.

In the above configuration, the barrier layer (12), specifically AlGaN layer, is recessed in a certain area at the source and drain non-ohmic contacts creating the open gate (17) around the 2DEG or 2DHG channel. This allows creating the round-shape microphone membrane design, as illustrated in FIG. 8c.

In a certain aspect, a hypersensitive microphone of embodiments contains an integrated PC-HEMT sensor comprising the following components:
the PC-HEMT of an embodiment, or an array thereof, wherein each one of said transistors is connected to its dedicated electrical contact line;
a battery connected to said electrical contact lines via an electric circuit for supplying electric current to said transistors;
an integrated or CMOS current amplifier connected to said battery for amplification of an electric current obtained from said transistors;
an analogue-to-digital converter (ADC) with in-built digital input/output card connected to said current amplifier for wirelessly outputting the converted signal to an external reading unit;
a wireless connection module for wireless connection of said microphone to the external reading and storage unit.

The external reading and storage unit may be any mobile device, desktop computer, server, remote storage, internet storage or internet-based cloud. In a specific embodiment, the wireless connection module can be a short-range Bluetooth or NFC providing wireless communication between the wearable device and a smartphone for up to 20 m. If this module is Wi-Fi, the connection can be established for up to 200 nm, while GSM allows the worldwide communication to the external device.

In some embodiments, the device of the present application can be used for portable long-time-operation solution within an industrial, medical, security or military setup. Since the device is intended for continuous use, it should have a very small power consumption saving the battery life for a prolong usage. This is one of the major reasons to use the non-ohmic high-resistive contacts connecting the PC-HEMT sensor to an electric circuit. The non-ohmic contacts actually limit an electric current flowing through the 2DEG channel by having an electrical resistance 3-4 times higher than the resistance of the 2DEG-channel, thereby reducing electrical power consumption without sacrificing sensitivity and functionality of the sensor. Thus, the use of non-ohmic contacts in some embodiments of the PC-HEMT sensor of the present application is a hardware solution allowing minimising the power consumption of the device. In another embodiment, the power consumption of the device can be minimised using a software algorithm managing the necessary recording time of the sensor and a battery saver mode, which limits the background data and switches the wireless connection only when it is needed.

The PC-HEMT sensor may also be integrated within the smartphone, smartwatch or any personal gadget or mobile device. It can be connected to the metallic chassis or to the capacitive sensitive display elements of the smartphone transducing an electrical charge to the sensor. The PC-HEMT sensor may also be installed (glued or attached) on any solid surface, such as indoor walls or ceilings or on any outdoor surface.

Example

Phonocardiography with the Microphone of Embodiments

The PC-HEMT sensor of the present invention can successfully replace a medical stethoscope used in listening to the internal sounds of a human heart (phonocardiography). Different heart abnormalities cause different heart sounds resulted from abnormal heart dynamics. The second heart sound (S2) is created by closing of the aortic valve followed by closing of the pulmonic valve. The physiological S2-split phenomena of the heart sound effect occurs during a deep inspiration and breath hold, where the second heart sound, which is normally observed as a single objective tone recorded with a stethoscope, is splitting into a two clearly separated sounds, conditional to normal activity of a healthy heart. Careful analysis of the splitting and intensity of the S2 can indicate the presence of many cardiovascular diseases. The splitting varies between zero and eighty milliseconds depending on the specific phase of the respiratory cycle. The aortic component of S2 (S2A) precedes the pulmonic component (S2P).

Using the PC-HEMT of embodiments allows to obtain the phonocardiography data from a patient. A series of experiments on recording electrical signals corresponding to physiological splits of the S2 heart sound, while the patient breathes in and out, from a single spot on the patient's breast, is demonstrated in this example. In contrast to the similar example in the patent application U.S. Ser. No. 15/067,093 describing the charge-sensitive mode of the sensor of embodiments for recording the phonocardiogram, the sensor of the present example acts in its pressure-sensitive mode capable of recording sound waves associated with the same phonocardiogram. The actual measurements were conducted for 30-45 sec with holding breath after each inspiration during the signal recording.

Figure 9:
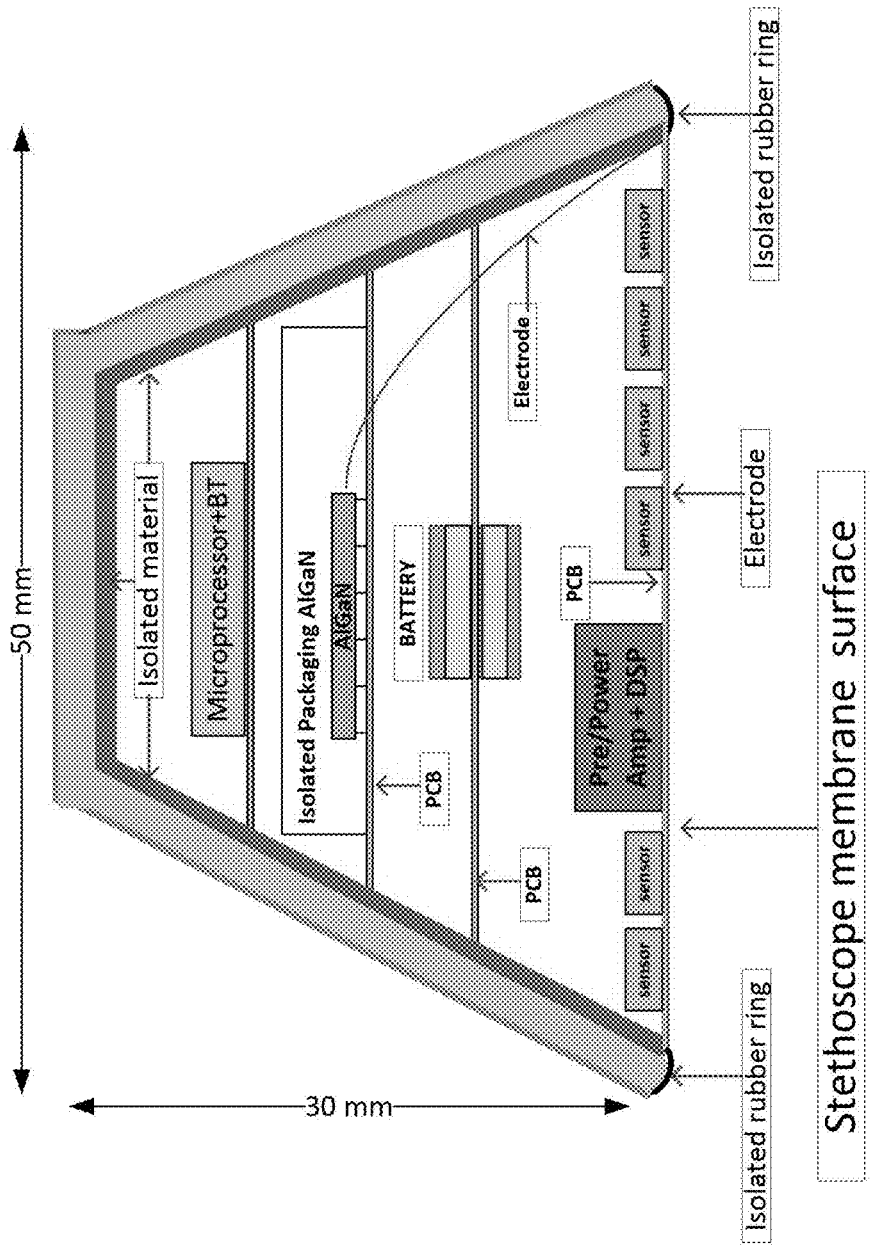
FIG. 9 schematically shows an exemplary stethoscope of the example.
Figure 10:
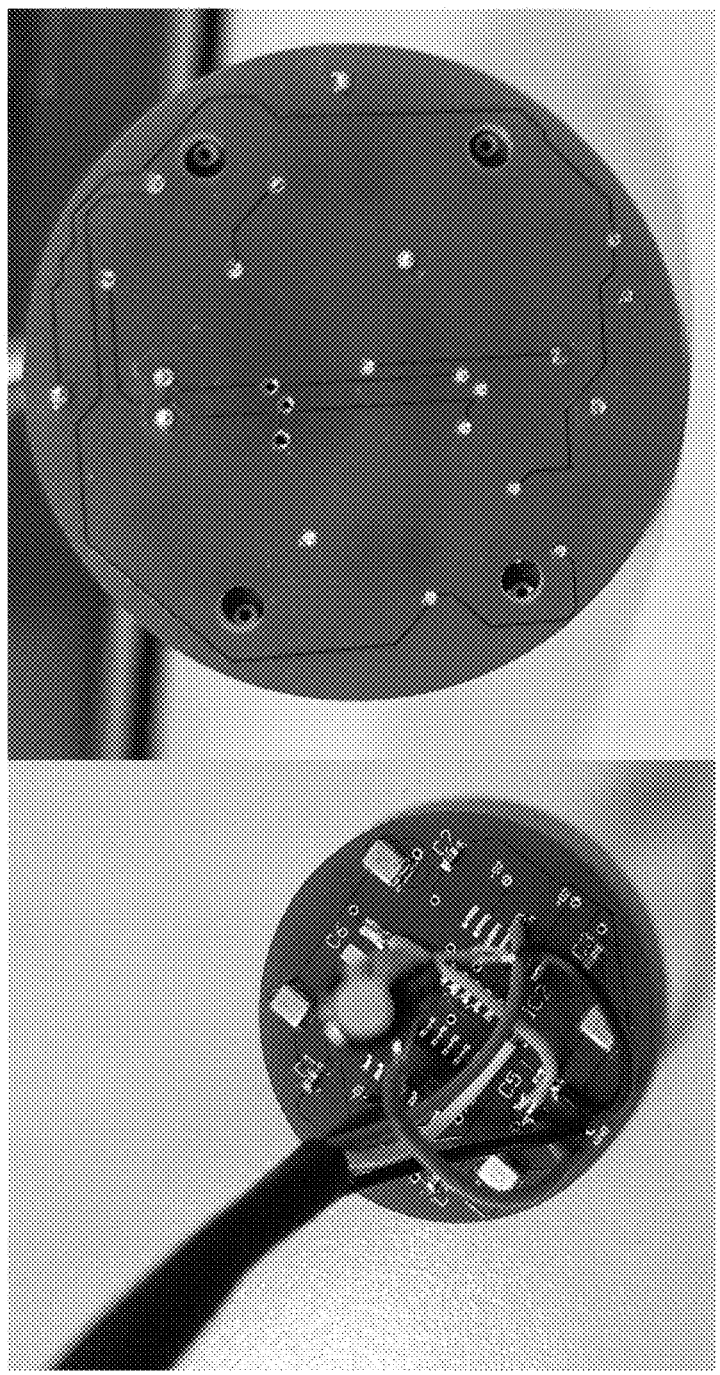
FIG. 10 shows the prototype first level PCB with the sensors and amplifier for the stethoscope shown in FIG. 9.
Figure 11A:
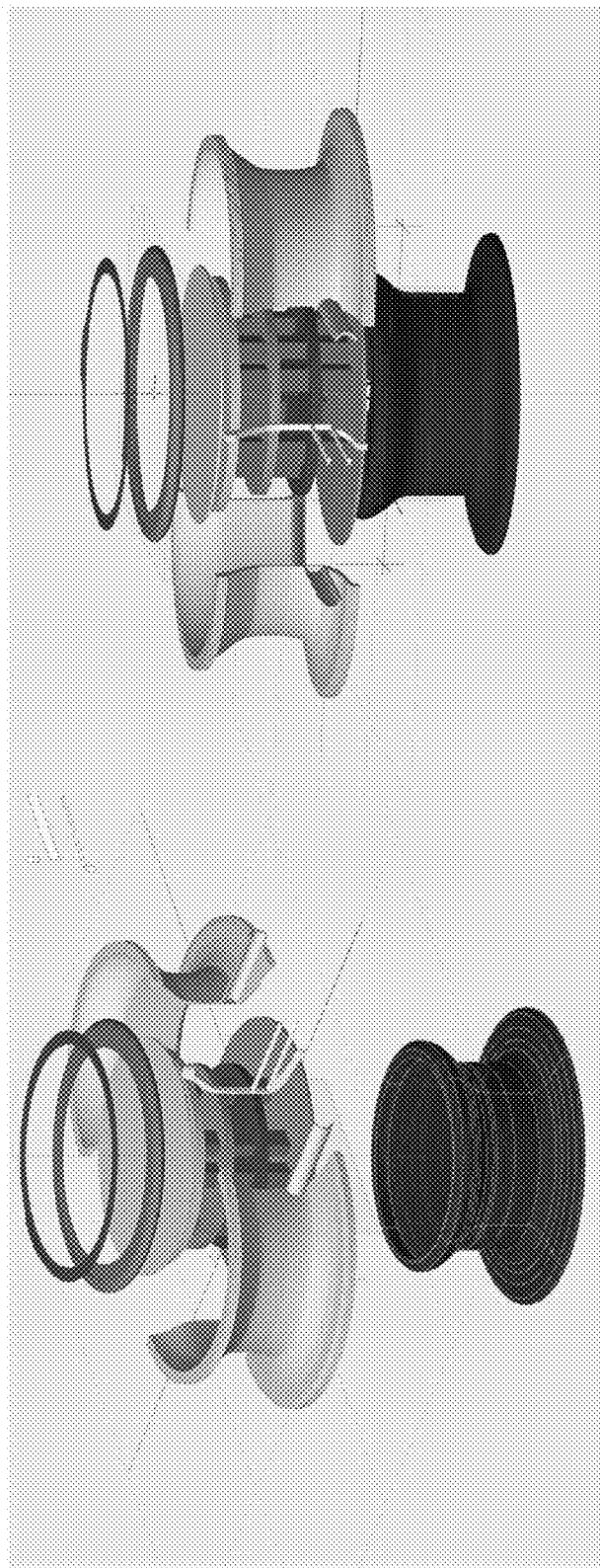

FIG. 9 schematically shows the exemplary stethoscope of the present example having an array of the PC-HEMTs installed on the printed circuit board (PCB) along with the integrated current amplifier and digital signal processor (DSP), and covered with a membrane. FIG. 10 shows the prototype first level PCB with the sensors and amplifier. The stethoscope design is shown in FIGS. 11a-11b.

Figure 12:
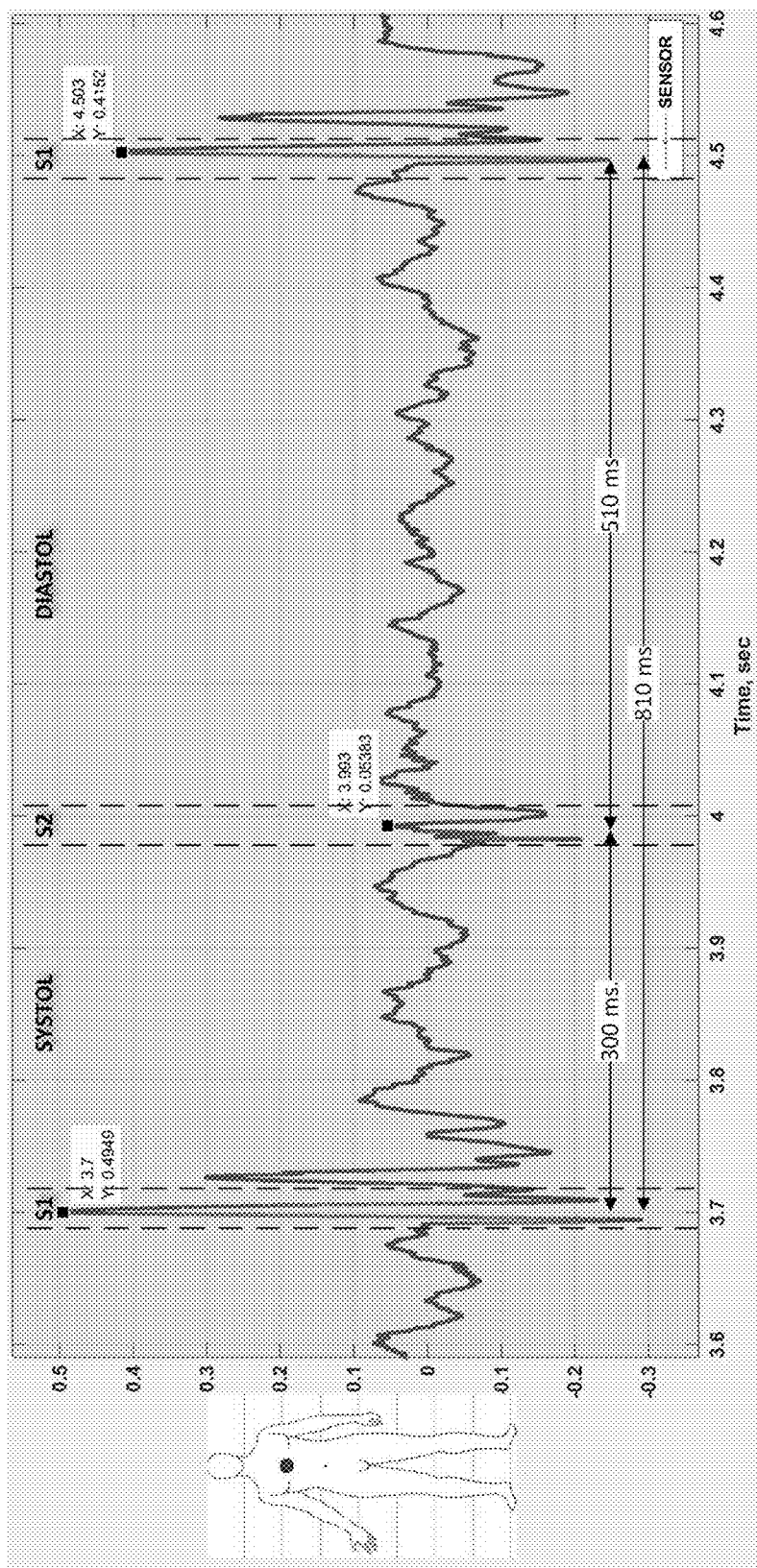
FIG. 12 shows the breath cycle recorded at a single body point during the normal breath rhythm and its expansion.

FIG. 12 shows the breath cycle recorded at a single body point during the normal breath rhythm and its expansion. The sound associated with the breath of a patient was recorded with the PC-HEMT sensor (placed on the first heart point) connected to the mic's Preamp DSP sound card at a sampling rate of 16 bit and frequency of 44.1 kHz. As clearly seen from FIG. 12, the split sounds S1 and S2 during the breath cycle can be easily identified.

Figure 13:
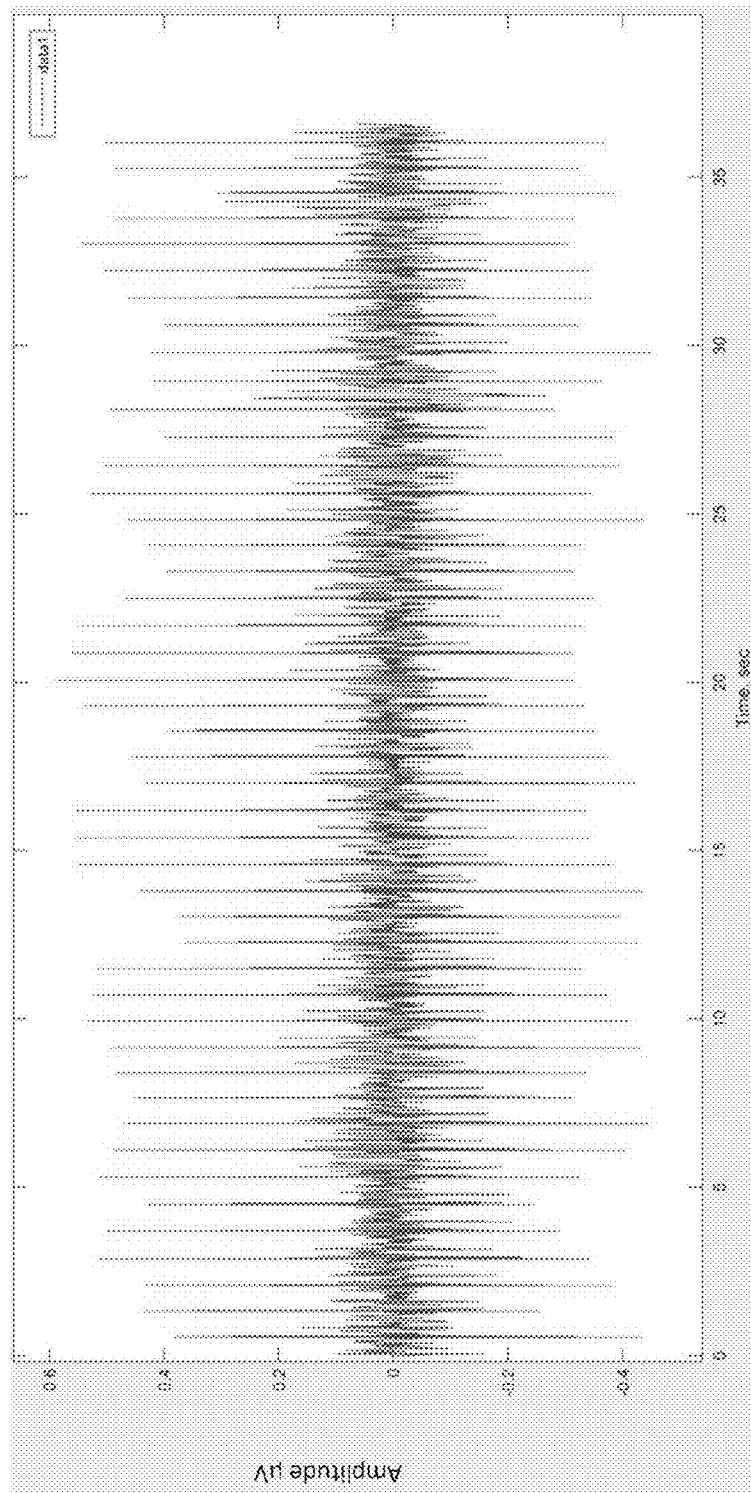
FIG. 13 shows the phonocardiogram recorded with the sensor of embodiments.
Figure 114A:
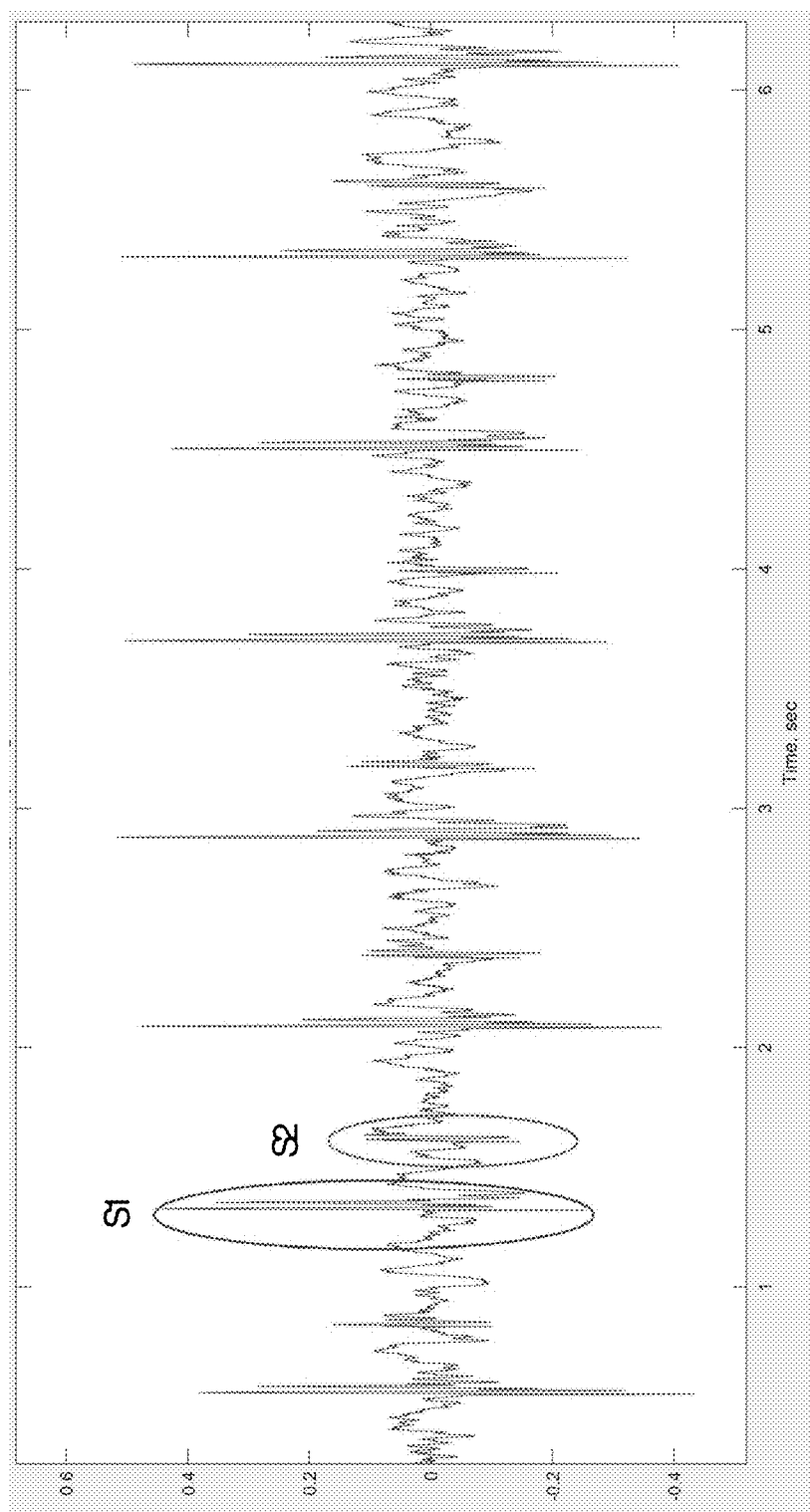
Figure 14B:
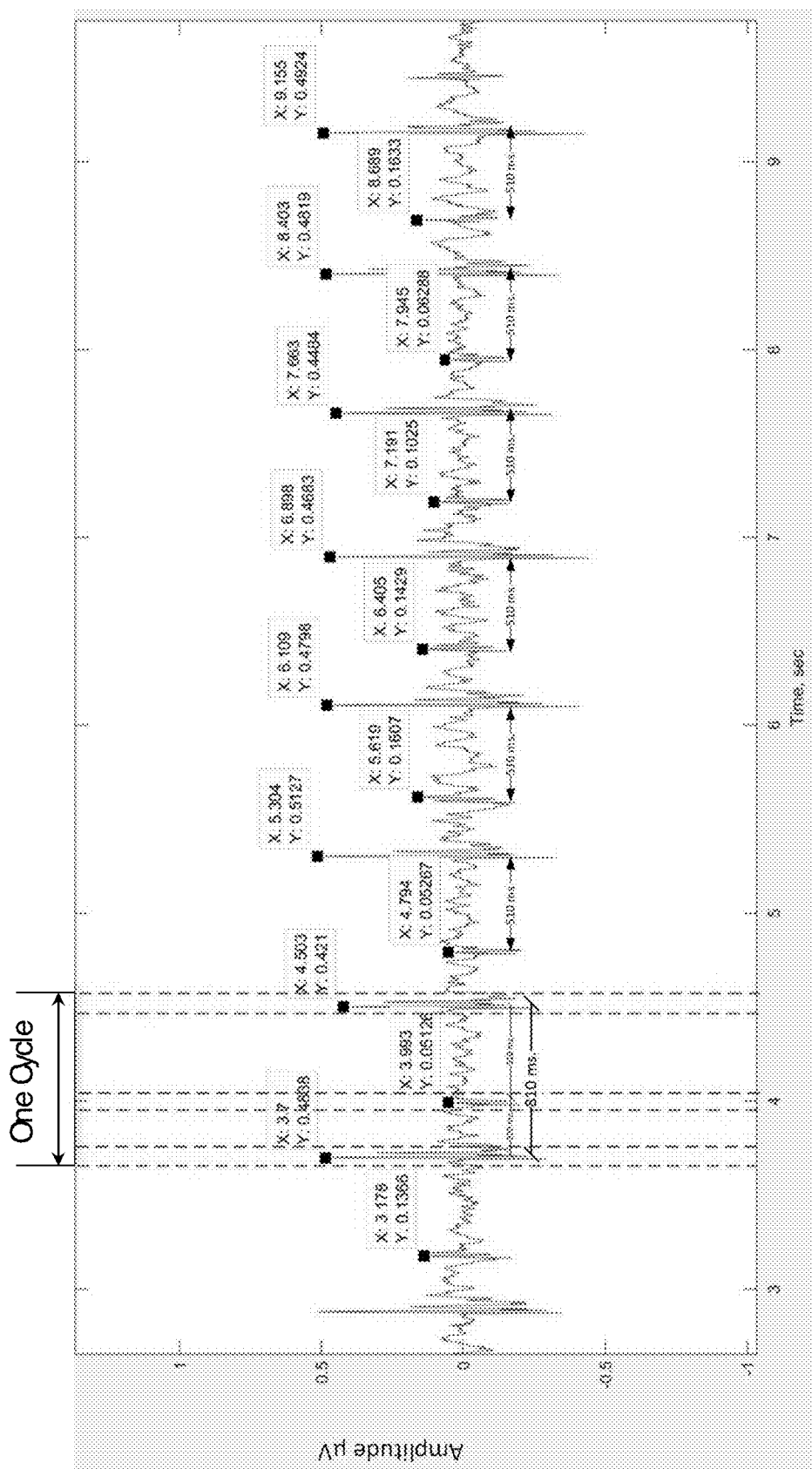
Figure 14C:
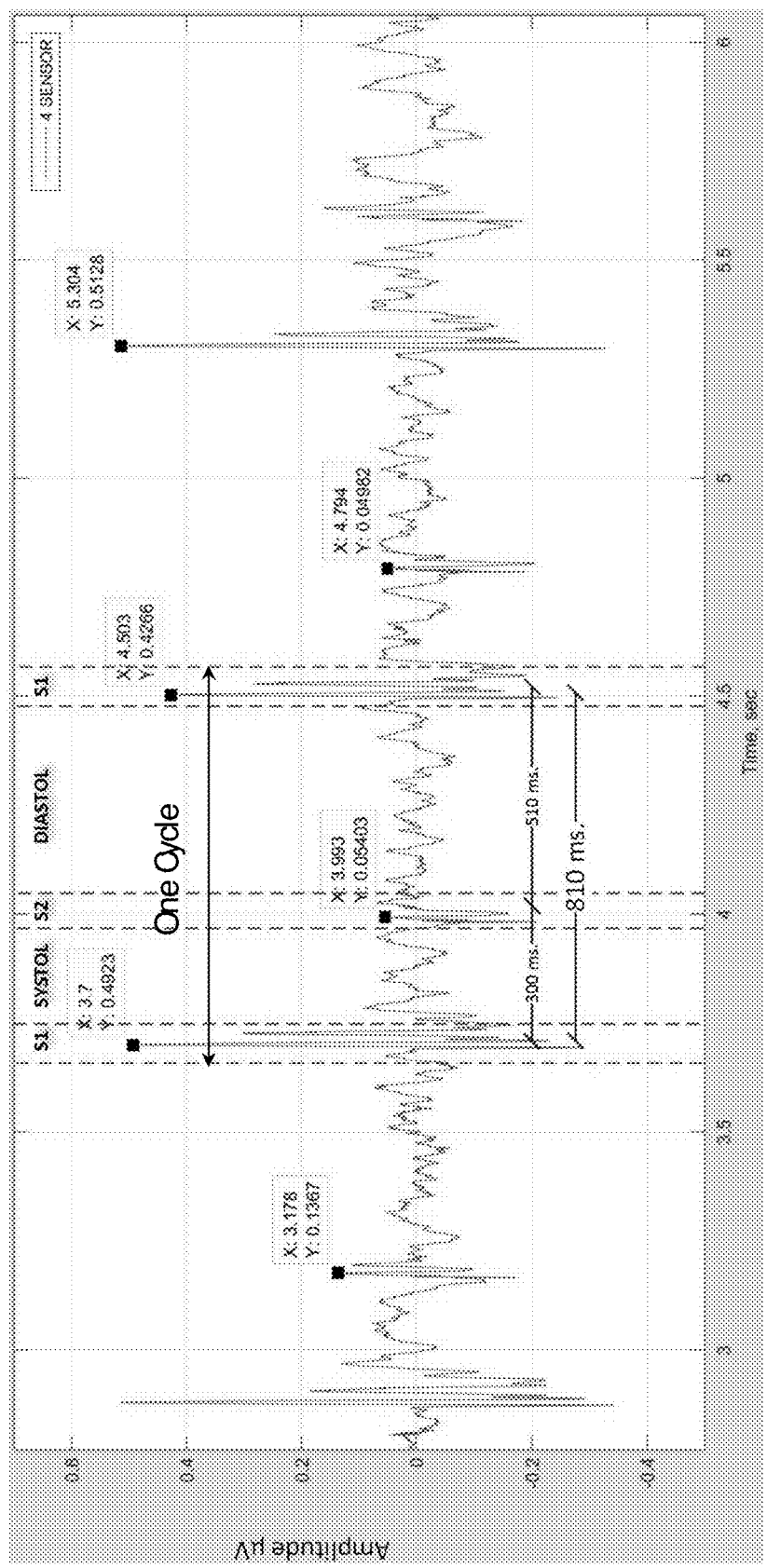

FIG. 13 shows the phonocardiogram recorded with the sensor of embodiments, while FIGS. 14a-14c show the expanded part of this phonocardiogram for 6-7 seconds in a zoom-in sequence. One breath cycle lasts for 810 milliseconds (ms). This is essentially the same breath cycle that is shown in FIG. 12.

The experimental results presented in FIGS. 12-14 also clearly demonstrates that the characteristic phonocardiogram S2-split into two peaks (A2-P2) correlates with the peak splitting recorded with the present sensor. The signals recorded with the sensor of embodiments clearly represent the differences between systolic and diastolic phases of the breath cycle. Thus, the PC-HEMT sensor can detect the S2-split phenomena and the whole breath dynamics using the sounds measurements at a single point on a patient's body and can be seen as a future substitute for a stethoscope.

While certain features of the present application have been illustrated and described herein, many modifications, substitutions, changes, and equivalents will be apparent to those of ordinary skill in the art. It is, therefore, to be understood that the appended claims are intended to cover all such modifications and changes as fall within the true spirit of the present application.

The invention claimed is:

1. A method for recording physiological sounds of a patient comprising:
   providing a microelectronic sensor comprising an open-gate pseudo-conductive high-electron mobility transistor or an array thereof, wherein said transistor comprises:
   a) a multilayer hetero-junction structure made of gallium nitride (GaN) and aluminium gallium nitride (AlGaN) single-crystalline or polycrystalline semiconductor materials, and placed on free-standing membranes, said structure comprising at least one buffer layer and at least one barrier layer, said layers being stacked alternately;
   b) a conducting channel comprising a two-dimensional electron gas (2DEG) or a two-dimensional hole gas (2DHG), formed at the interface between said buffer layer and said barrier layer, and upon applying a bias to said transistor, becoming capable of providing electron or hole current, respectively, in said transistor between source and drain contacts; and
   c) the source and drain contacts connected to said 2DEG or 2DHG conducting channel and to electrical metallisations for connecting said transistor to an electric circuit;
   said transistor is characterised in that the thickness of a top layer of said heterojunction structure in the open gate area is 5-9 nanometres (nm) and the surface of said top layer has a roughness of 0.2 nm or less, wherein the combination of said thickness and said roughness of the top layer creates a quantum electronic effect of operating said 2DEG or 2DHG channel simultaneously in both normally-on and normally-off operation modes of the channel, thereby making said transistor to conduct electric current through said channel in a quantum well between normally-on and normally-off operation modes of the transistor;
   contacting a single sensing point on the patient's body with, or remotely positioning in a space against the patient's body, said microelectronic sensor;
   recording electrical signals received from the patient's body in a form of a source-drain electric current of said transistor over time (defined as $I_{DS}$ dynamics) with said microelectronic sensor;
   transmitting the recorded signals from said microelectronic sensor to an external memory for further processing; and
   processing the transmitted signals in the external memory, correlating said $I_{DS}$ dynamics with the physiological sounds and extracting the physiological sounds from said transmitted signals in a form of medical data, thereby obtaining physiological sound records.

2. The method of claim 1, wherein said recorded physiological sound is a heart split sound, the first heart sound (S1) or the second heart sound (S2).

3. The method of claim 1, wherein said medical data is associated with a phonocardiogram.

4. The method of claim 1, wherein said single sensing point on the patient's body is a patient's breast.

5. The method of claim 1, wherein said microelectronic sensor is contactless and used remotely from the patient's body, being positioned in a space against the patient's body.

6. The method of claim 1, wherein the source and drain contacts of said transistor are ohmic.

7. The method of claim 1, wherein the electrical metallizations of the transistor are capacitively coupled to the 2DEG or 2DHG conducting channel for inducing displacement currents, thus resulting in said source and drain contacts being non-ohmic.

8. The method of claim 1, wherein the transistor further comprises a dielectric layer deposited on top of the multilayer hetero-junction structure of the transistor.

9. The method of claim 1, wherein the free-standing membranes, on which the multilayer hetero-junction structure of the transistor is placed, are free-standing columns of substrate composed of sapphire, silicon, silicon carbide, gallium nitride or aluminium nitride.

10. The method of claim 1, wherein the thickness of the top layer (GaN or AlGaN) of the transistor in the open gate area is 6-7 nm.

11. The method of claim 10, wherein the thickness of said top layer in said open gate area is 6.2 nm to 6.4 nm.

12. The method of claim 1, wherein said top layer has the roughness of about 0.1 nm or less, or 0.05 nm or less.

13. The method of claim 1, wherein said substrate is gallium nitride (GaN) having a thickness of 0.5-2 µm.

14. The method of claim 1, wherein the transistor or the array thereof is printed on a flexible printed circuit board, and each one of said transistors is connected to its dedicated electrical contact line printed on said flexible printed circuit board.

15. The method of claim 1, wherein said external memory is a smartphone, smartwatch or any other personal gadget or mobile device, a desktop computer, server, remote storage, internet storage or network cloud.

16. The method of claim 10, wherein said top layer has the roughness of about 0.1 nm or less, or 0.05 nm or less.

17. The method of claim 1, wherein said multilayer hetero-junction structure comprises:
   A. (i) one top AlGaN layer recessed in an open gate area of the transistor to the thickness of 5-9 nm and having the surface roughness of 0.2 nm or less, and (ii) one bottom GaN buffer layer; said layers have Ga-face polarity, thus forming the two-dimensional electron gas (2DEG) conducting channel in said GaN layer, close to the interface with said AlGaN layer; or
   B. (i) one top GaN layer recessed in an open gate area of the transistor to the thickness of 5-9 nm and having the surface roughness of 0.2 nm or less, (ii) one bottom GaN buffer layer, and (iii) one AlGaN barrier layer in between; said layers have Ga-face polarity, thus forming a two-dimensional hole gas (2DHG) conducting channel in the top GaN layer, close to the interface with said AlGaN barrier layer; or
   C. (i) one top GaN layer recessed in an open gate area of the transistor to the thickness of 5-9 nm and having the surface roughness of 0.2 nm or less, (ii) one bottom GaN buffer layer, and (iii) one AlGaN barrier layer in between; said layers have N-face polarity, thus forming a two-dimensional electron gas (2DEG) conducting channel in the top GaN layer, close to the interface with said AlGaN barrier layer; or D) (i) one top AlGaN layer recessed in an open gate area of the transistor to the thickness of 5-9 nm and having the surface roughness of 0.2 nm or less, and (ii) one bottom GaN buffer layer; said layers have N-face polarity, thus forming a two-dimensional hole gas (2DHG) conducting channel in the GaN buffer layer, close to the interface with said AlGaN barrier layer.

18. A hypersensitive microphone for recording physiological sounds comprising the microelectronic sensor of claim 1.

19. The microphone of claim 18, wherein said microphone is suitable for being integrated within a smartphone, a smartwatch or any personal gadget or mobile device.

20. The microphone of claim 18, wherein said microphone is suitable for being integrated within a stethoscope.

21. The microphone of claim 18, wherein said microphone is suitable for being integrated within a hearing aid.

* * * * *